(12) United States Patent
Zamolodchikov et al.

(10) Patent No.: US 10,295,550 B2
(45) Date of Patent: May 21, 2019

(54) COMPOSITIONS AND METHODS FOR USE IN DIAGNOSIS OF ALZHEIMER'S DISEASE

(71) Applicant: The Rockefeller University, New York, NY (US)

(72) Inventors: Daria Zamolodchikov, New York, NY (US); Sidney Strickland, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 15/527,464

(22) PCT Filed: Nov. 17, 2015

(86) PCT No.: PCT/US2015/060996
§ 371 (c)(1),
(2) Date: May 17, 2017

(87) PCT Pub. No.: WO2016/081413
PCT Pub. Date: May 26, 2016

(65) Prior Publication Data
US 2017/0363644 A1    Dec. 21, 2017

Related U.S. Application Data

(60) Provisional application No. 62/080,707, filed on Nov. 17, 2014.

(51) Int. Cl.
*G01N 33/53* (2006.01)
*G01N 33/566* (2006.01)
*G01N 33/567* (2006.01)
*G01N 33/68* (2006.01)
*C07K 7/08* (2006.01)
*C07K 7/18* (2006.01)
*C07K 16/18* (2006.01)

(52) U.S. Cl.
CPC .......... *G01N 33/6896* (2013.01); *C07K 7/08* (2013.01); *C07K 7/18* (2013.01); *C07K 16/18* (2013.01); *C07K 2317/33* (2013.01); *G01N 2800/2821* (2013.01)

(58) Field of Classification Search
None
See application file for complete search history.

(56) References Cited

U.S. PATENT DOCUMENTS

| | | |
|---|---|---|
| 2005/0260681 A1 | 11/2005 | McIntyre |
| 2009/0202980 A1 | 8/2009 | Gebbink et al. |
| 2011/0129859 A1 | 6/2011 | Tsubouchi et al. |

*Primary Examiner* — Olga N Chernyshev
(74) *Attorney, Agent, or Firm* — Hodgson Russ LLP

(57) ABSTRACT

Provided are compositions and methods useful in the diagnosis of Alzheimer's Disease (AD). The methods involve immunologically testing biological samples for an amount of high molecular weight kininogen (HK) and cleaved high molecular weight kininogen (HKc), wherein determining less HK relative to a normal control, or determining more HKc relative to a normal control, or a combination thereof, aids in diagnosis of AD. Hybridomas and monoclonal antibodies bind with specificity to either HK alone, or to both HK and HKc. Kits for use in immunological AD testing using the mAbs are also provided.

3 Claims, 20 Drawing Sheets
Specification includes a Sequence Listing.

ELISA design

Figure 27

Pre-clearing samples of intact HK to detect HKc

Step 1: Pre-clear plasma with 2B7 (specific for intact HK)

Step 2: Transfer pre-cleared plasma to new plate coated with 3E8 which binds both HK and HKc, but as depicted will bind HKc remaining in plasma - assuming complete depletion of HK)

Step 3: Determine remaining HKc in sample using 6A6B, 12E5A, or 15D9, which detect both HKc and HK, but as depicted here will detect HKc captured by 3E8)

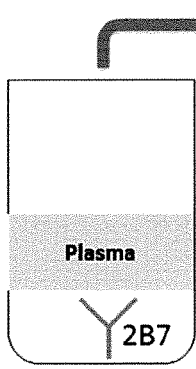
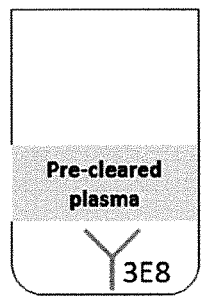
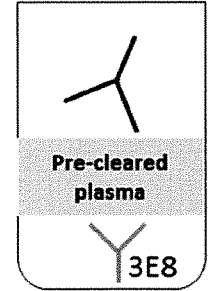

COMPOSITIONS AND METHODS FOR USE IN DIAGNOSIS OF ALZHEIMER'S DISEASE

CROSS-REFERENCE TO RELATED APPLICATIONS

This application claims priority to U.S. patent application No. 62/080,707, filed Nov. 17, 2014, the disclosure of which is incorporated herein by reference.

STATEMENT REGARDING FEDERALLY SPONSORED RESEARCH

This invention was made with government support under contract no. NS50537 awarded by the National Institutes of Health. The government has certain rights in the invention.

FIELD

The present disclosure relates generally to diagnosis of Alzheimer's Disease (AD) and more specifically to compositions and methods related to measurement of plasma levels of activated factor XII and cleaved high molecular weight kininogen for use in AD diagnosis.

BACKGROUND

Alzheimer's disease (AD) represents an enormous and growing public health problem, due in large part to the fact that there are no effective therapies. A major roadblock to the treatment of AD is the lack of adequate diagnostic tools. Diagnosis is generally based on cognitive decline, which is not necessarily specific to AD. Furthermore, clinically-measurable cognitive decline in AD is thought to manifest after significant neuronal damage has already occurred, precluding the implementation of treatments at early stages of disease before irreversible neuronal damage has taken place. Current methods of diagnosis that allow early detection of AD (brain imaging to detect amyloid-beta (Aβ) deposits and measurement of cerebrospinal fluid levels of Aβ) are expensive, invasive, and have limited availability. An accessible plasma biomarker that provides an AD diagnosis at early stages of disease would therefore be of great benefit to assist with AD diagnosis. The present disclosure meets these and other needs.

SUMMARY

The present disclosure provides compositions and methods for diagnosis and/or aiding in the diagnosis of AD. This disclosure is based in part on our demonstration that AP can activate factor XII (FXII) in purified protein systems, human plasma, and mouse plasma, and that Aβ-mediated activation of FXII initiates the blood clotting cascade and inflammatory processes. Further, this disclosure includes the first demonstration that plasma from AD patients contains increased levels of activated FXII (FXIIa) when compared to plasma from normal (non-demented) subjects, and lower levels of the FXIIa substrate high molecular weight kininogen (HK). Thus, determining cleavage of HK into its cleaved form (HKc) is herewith demonstrated to be a sensitive tool for measuring FXII activation. Our results suggest that the Aβ-mediated activation of FXII observed in vitro also occurs in AD patient plasmas. Thus, the present disclosure provides a variety of approaches and reagents for testing for activation of FXII using HK and HKc, as well as fragments thereof, as markers in convenient blood tests to help diagnose patients with AD. In embodiments the fragments are degradation products of HK and/or HKc. In an embodiment, the fragment comprises or consists of Domain 5 of HK/HKc.

In embodiments, the disclosure includes testing a biological sample obtained from a subject suspected of having or at risk for developing AD for the presence and/or amounts of HK and HKc. In general, determining more HKc relative to a normal control, and/or or less HK relative to a normal control aids in diagnosis of AD. Conversely, determining similar HKc and/or similar HK relative to a normal control, aids in a diagnosis of the individual as not having AD.

Any suitable biological sample can be used for testing. In one embodiment, a sample of plasma is tested. In embodiments, the sample does not comprise cerebrospinal fluid.

In embodiments the sample is tested using any suitable immunological approach that can determine qualitatively or quantitatively the amount of HK and/or HKc in a sample. In embodiments, the disclosure comprises enzyme-linked immunosorbent assay (ELISA) based approaches. These assays can be carried out using novel antibodies or antigen binding fragments thereof generated using the compositions and methods described herein. Such antibodies will discriminate HK from HKc, and in certain embodiments may discriminate HK and HKc from smaller fragments of HK. Thus, the disclosure includes making and using an antibody and/or antigen binding fragment thereof that binds with specificity to HK only, or to HKc only, or to both HK and HKc. The antibodies are generated initially by immunizing non-human animals using full length HK, or full length HKc, or polypeptide fragments of HK and HKc as further described in the amino acid sequences presented in this disclosure. Distinct antibodies and antigen binding fragments thereof generated and used according to this disclosure will bind with specificity to at least one epitope that is unique to HK, and at least one epitope that is unique to HKc, and to at least one epitope that is common to HK and HKc. In embodiments, certain antibodies do not bind to low molecular weight kininogen (LK) as described in more detail below.

Per convention, monoclonal antibodies (mAbs) and the hybridomas that produce them are referred to herein using the same term. In particular embodiments, disclosure encompasses antibodies produced by the hybridoma referred to as "3E8." As described further below, the 3E8 mAb binds with specificity to both HK and HKc. 3E8 can accordingly be used in a variety of immunological detection assays to separate HK and HKc from, for example, a biological fluid. In embodiments, 3E8 can be used as a capture antibody in, for example, an ELISA assay. The 3E8 mAb was obtained by immunization of hamsters using the peptide corresponding to residues 563-581, where amino acid numbering excludes the signal peptide) of human high molecular weight kininogen. The immunogen has the sequence: IQSDDDWIPDIQIDPNGLSC (SEQ ID NO:6). The terminal cysteine is added to the native sequence for coupling. Thus, in an embodiment, the disclosure includes a mAb that binds with specificity to a peptide consisting of the sequence of SEQ ID NO:6. The disclosure also includes mAb and hybridoma 2B7, which binds with specificity to HK only, and therefore does not bind with specificity to HKc. To obtain 2B7, purified full length human HK and HKc were injected into hamsters and hybridomas were produced and screened to identify those producing mAbs that recognize HK but not HKc in solution.

In other examples, the disclosure includes hybridomas and mAbs produced by them which are termed 6A6-B, 12E5-A, and 15D9. Each of these bind with specificity to both HK and HKc. Thus, they are suitable for using, for example, as detection antibodies for total HK (HK+HKc) measurements, and for detection of HKc following clearance of samples with, for example, 2B7. A non-limiting and representative ELISA assay schematic using mAbs of this disclosure is shown in FIG. 21. A non-limiting and representative combined ELISA/clearance schematic using mAbs of this disclosure is shown in FIG. 27.

In one aspect the disclosure includes a method for aiding in diagnosis of AD by testing a human plasma sample in an ELISA assay for HKc and/or HK in or from the sample. This comprises an ELISA assay that employs a capture antibody that binds with specificity to both HK and HKc (but not to LK) and a detection antibody that binds with specificity to HKc but not to HK. In another aspect the disclosure includes a method for aiding in diagnosis of AD by testing a human plasma sample in an ELISA assay for HK in or from the sample. This comprises an ELISA assay that employs a capture antibody that binds with specificity to both HK and HKc (but not to LK) and a detection antibody binds with specificity to HK, but does not bind with specificity to HKc. Combinations of such assays are included and provide for ascertaining the relative amounts of HK to HKc. Alternatively or additionally the amounts of HK and HKc can be compared to any suitable reference.

Articles of manufacture, such as kits, comprising the antibodies and antigen binding fragments thereof are also included. These comprise a container for holding antibodies or antigen binding fragments thereof, and can further comprise packaging. The packaging can include printed material, such as a label or paper insert, which provides information about use of the antibodies or antigen binding fragments thereof and related reagents for immunondiagnostic processes used to aid in the diagnosis of AD, or for measuring HK and HKc.

Hybridomas that produce the antibodies are included in the disclosure, as are recombinant methods of producing the antibodies and antigen binding fragments of them. As such the disclosure includes expression vectors which encode the antibodies or encode at least the complementarity determining regions (CDRs) of the antibodies. Cell cultures which comprise the expression vectors, and methods of expressing and separating the antibodies and antigen binding fragments thereof from the cell cultures are also included.

and FXI-deficient human plasma (FXI-def) show that the band just above the FXI band is non-specific. (B) FXI levels normalized to transferrin were lower in AD than ND plasma (p=0.008). Levels of FXIIa normalized to transferrin in these samples were as determined in Examples 1-6, and mean values for each group are designated by asterisk. (C) C1inh levels were lower in AD than ND plasma (p=0.0008). Levels of FXIIa normalized to transferrin in these samples were determined in Examples 1-6, and mean values for each group are designated by asterisk. (D) Levels of FXI, C1inh, and transferrin were analyzed in 10 AD and 10 ND plasmas from Group 2. (E) FXI levels were lower in AD than ND plasma (p=0.0003). (F) C1inh levels were lower in AD than ND plasma (p=0.01). (G) Levels of fibrin monomer were analyzed under reducing conditions in 10 AD and 10 ND plasma samples from Group 2 using antibody 59D8 specific for fibrin beta chain. (H) D-dimer levels were analyzed under non-reducing conditions in 10 AD and 10 ND plasma samples from Group 2. (I) Fibrin (p=0.009) and D-dimer (p=0.018) levels were increased in Group 2 AD plasma compared to control. (J) Fibrin (r=−0.49; p=0.03) and D-dimer (r=−0.57, p=0.008) levels were negatively correlated with FXI levels in samples from Group 2 as described in the Example which this figure accompanies.

Figure 17:
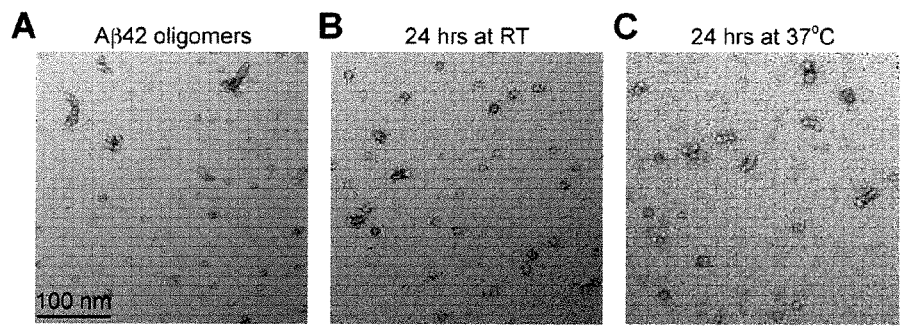

FIG. 17. Stability of Aβ42 oligomers. (A) Aβ42 oligomers were prepared as described in Methods and imaged by Transmission Electron Microscopy (TEM) as follows: samples were diluted to 0.1 mg/ml, applied to glow discharged CF200-Cu grids (Electron Microscopy Sciences), washed three times with ultrapure water (UV-treated with a Millipore system), and negatively stained with 2% uranyl acetate. Images were acquired using a JEOL JEM 100CX Transmission Microscope at The Rockefeller University Electron Microscopy Resource Center. (B) Aβ42 oligomers imaged after incubation for 24 hours at RT. (C) Aβ42 oligomers imaged after incubation for 24 hours at 37° C.

Figure 18:
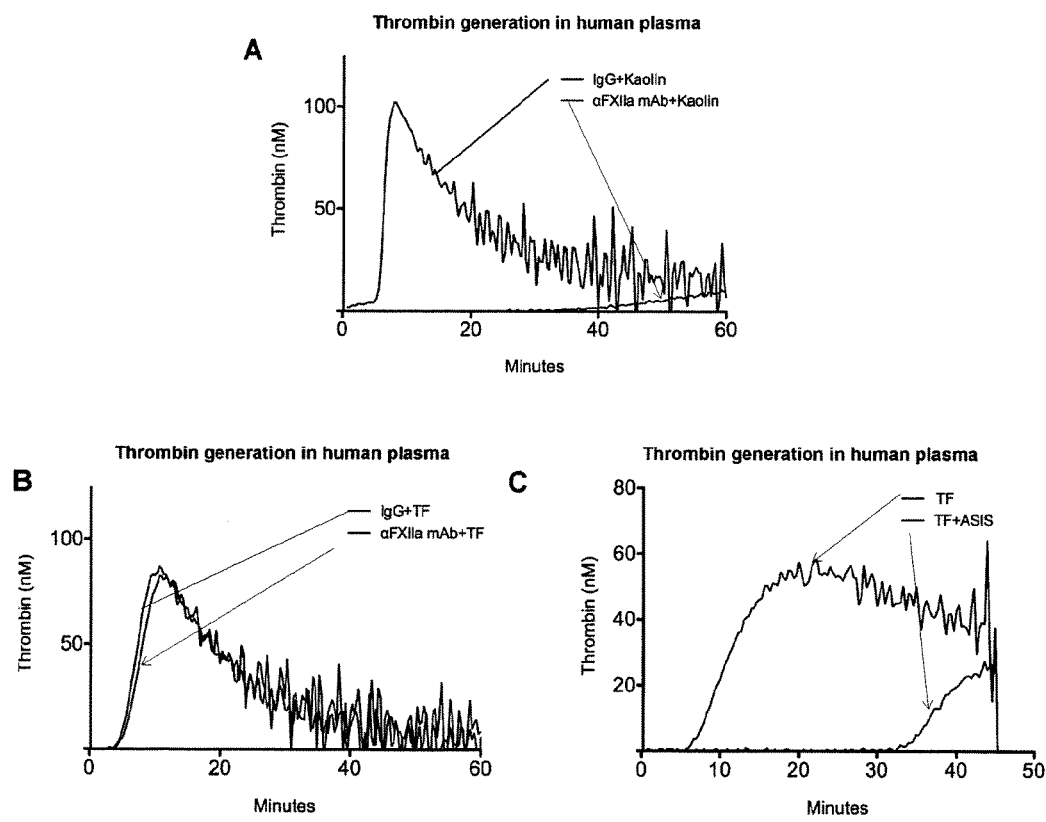

FIG. 18. Efficacy of the anti FXIIa function-blocking antibody and active site inhibited factor VII (ASIS). Functionality of the anti-FXIIa antibody and ASIS were evaluated via CAT. (A) Platelet poor plasma was pre-incubated with the anti-FXIIa antibody or control IgG for 30 minutes, and thrombin initiated by kaolin (10 µg/ml), an activator of FXII. The anti-FXIIa antibody completely blocked kaolin-mediated thrombin generation, confirming its ability to block FXIIa. (B) Platelet poor plasma was pre-incubated with the anti-FXIIa antibody or control IgG for 40 minutes, and thrombin generation initiated by tissue factor (TF; Thrombinoscope BV; 0.5 pM), an activator of the extrinsic coagulation pathway. The anti-FXIIa antibody had no effect on TF-mediated thrombin generation, confirming its specificity for blocking the FXIIa-driven intrinsic coagulation pathway. (C) Platelet poor plasma was pre-incubated with ASIS (60 nM), which blocks TF-mediated thrombin generation, and thrombin generation was initiated by adding 0.5 pM TF. ASIS blocked TF-mediated thrombin generation.

Figure 19:
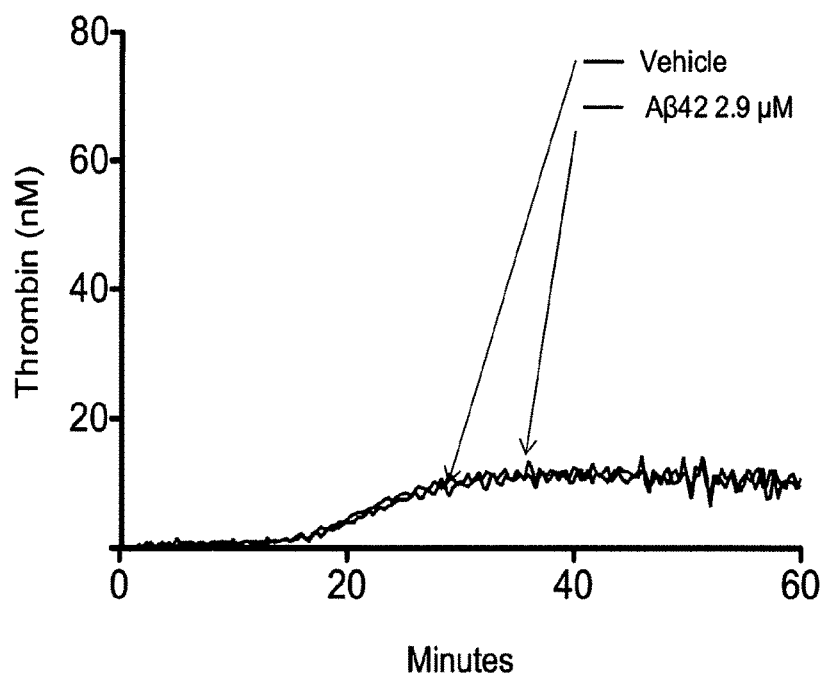

FIG. 19. Aβ42 fails to trigger thrombin generation in plasma from FXI−/− mice. Thrombin generation in FXI−/− plasma as measured by CAT. Aβ42 had no effect on thrombin generation.

Figure 20:
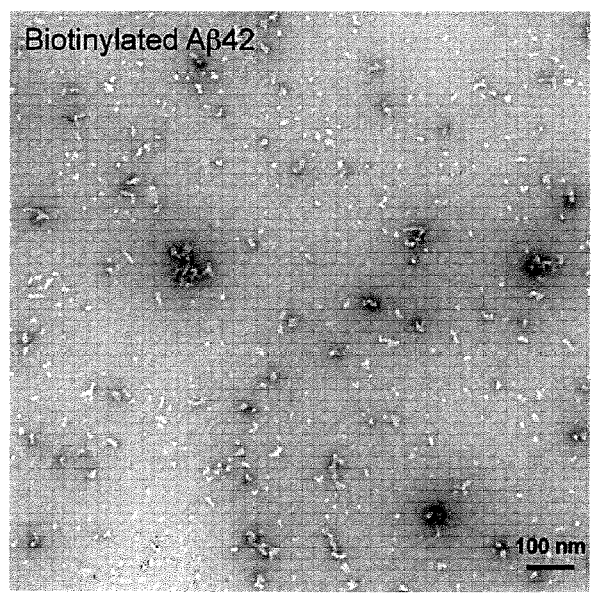

FIG. 20. Biotinylated Aβ42 forms oligomers. N-terminally biotinylated Aβ42, similar to preparations used for pulldown assay imaged by TEM.

Figure 21:
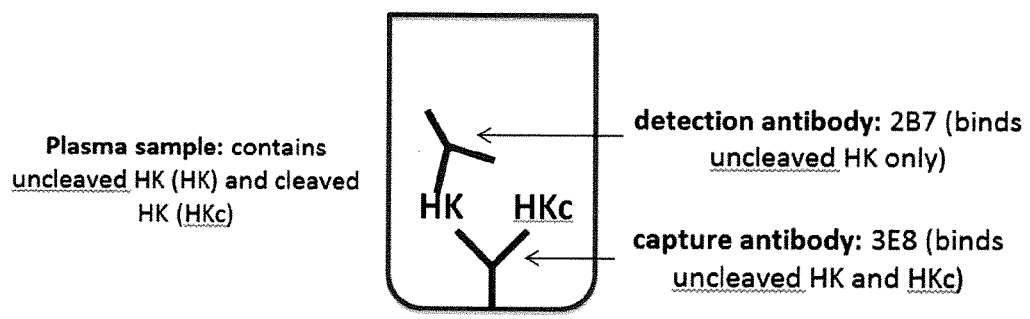

FIG. 21. ELISA schematic. A representative ELISA embodiment for detection of intact HK in human plasma. As illustrated, the ELISA comprises use of a capture antibody that binds both HK and HKc, a plasma sample containing a mixture of HK and HKc, and a labeled detection antibody that only detects HK. The ELISA determines the amount of HK in the sample based on a reference, such as a standard curve obtained using purified HK. The ELISA may or may not be combined with another ELISA determining the total amount of HK (HK+HKc) in the plasma sample, from which the amount of intact HK can be subtracted to determine HKc levels.

Figure 22:
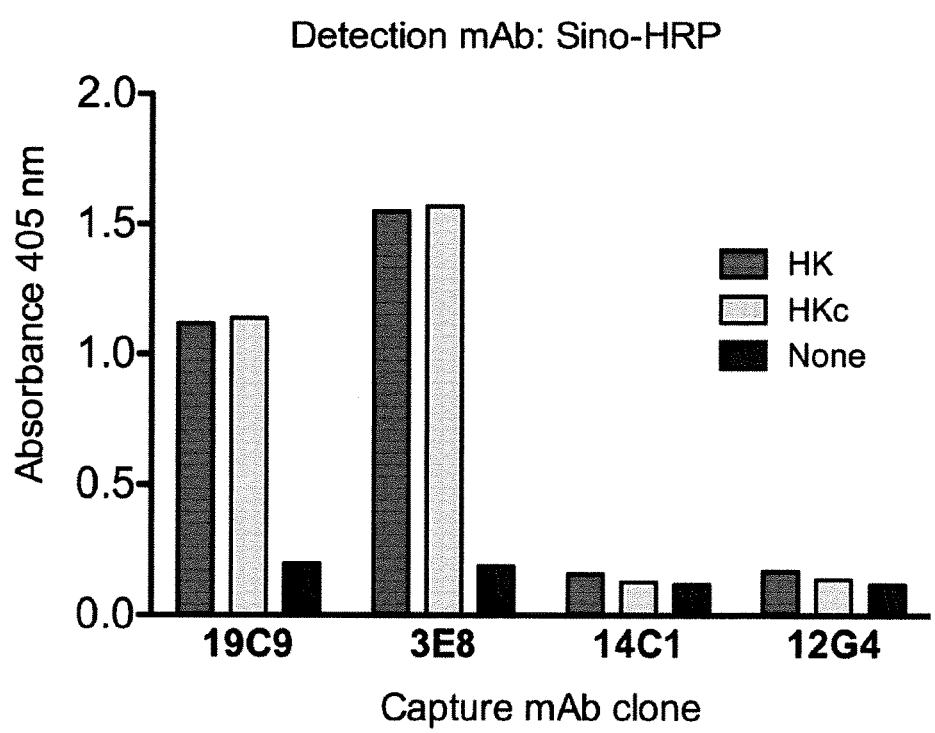

FIG. 22. ELISA capture antibody test. Antibodies from conditioned media of 4 different hybridoma lines were immobilized on Protein G plates, and the antibodies were exposed to HK, HKc, or buffer. A commercially available HRP-conjugated detection antibody was then used to quantify the amount of HK or HKc captured.

Figure 23:
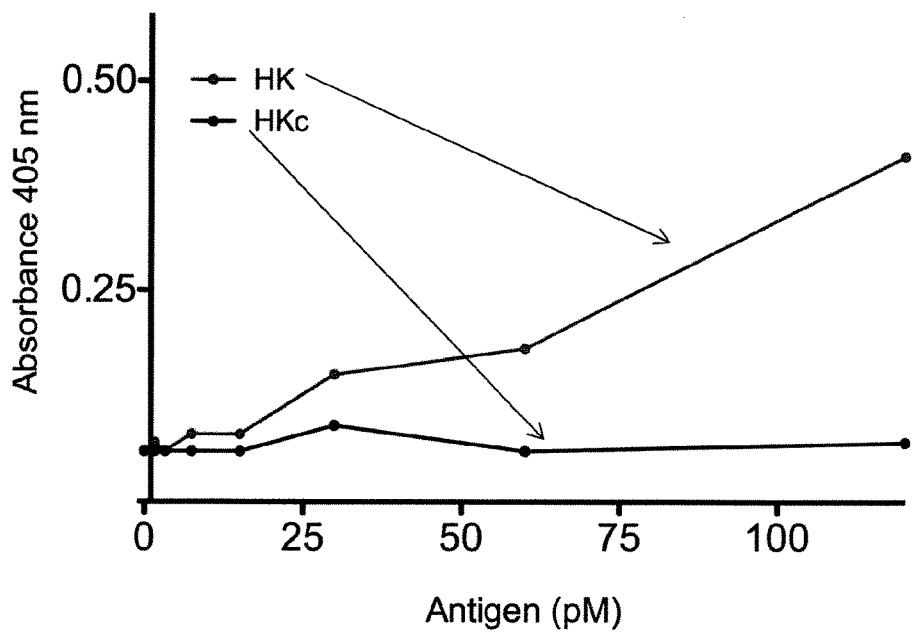

FIG. 23. ELISA detection antibody test in a purified protein system. Antibody 2B7 detects HK but not HKc captured on antibody 3E8. A standard curve using purified HK and HKc is shown.

Figure 24:
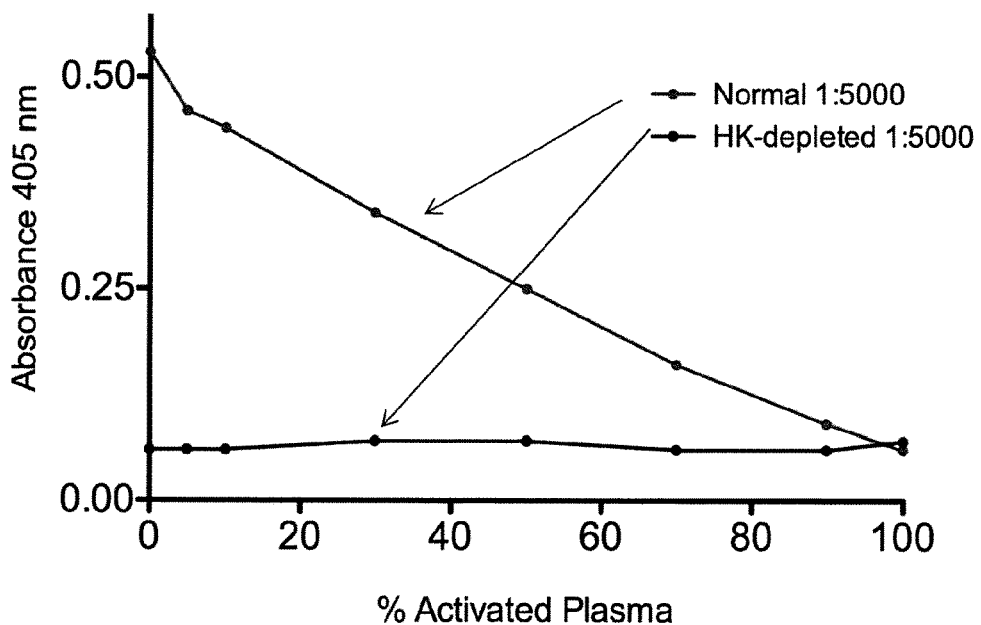

FIG. 24. ELISA detection antibody test in human plasma. Antibody 2B7 detects HK but not HKc captured on antibody 3E8 in normal but not HK-depleted human plasma. The more activated plasma is in the sample, the less intact HK is present (and the more HKc is present).

Figure 1:
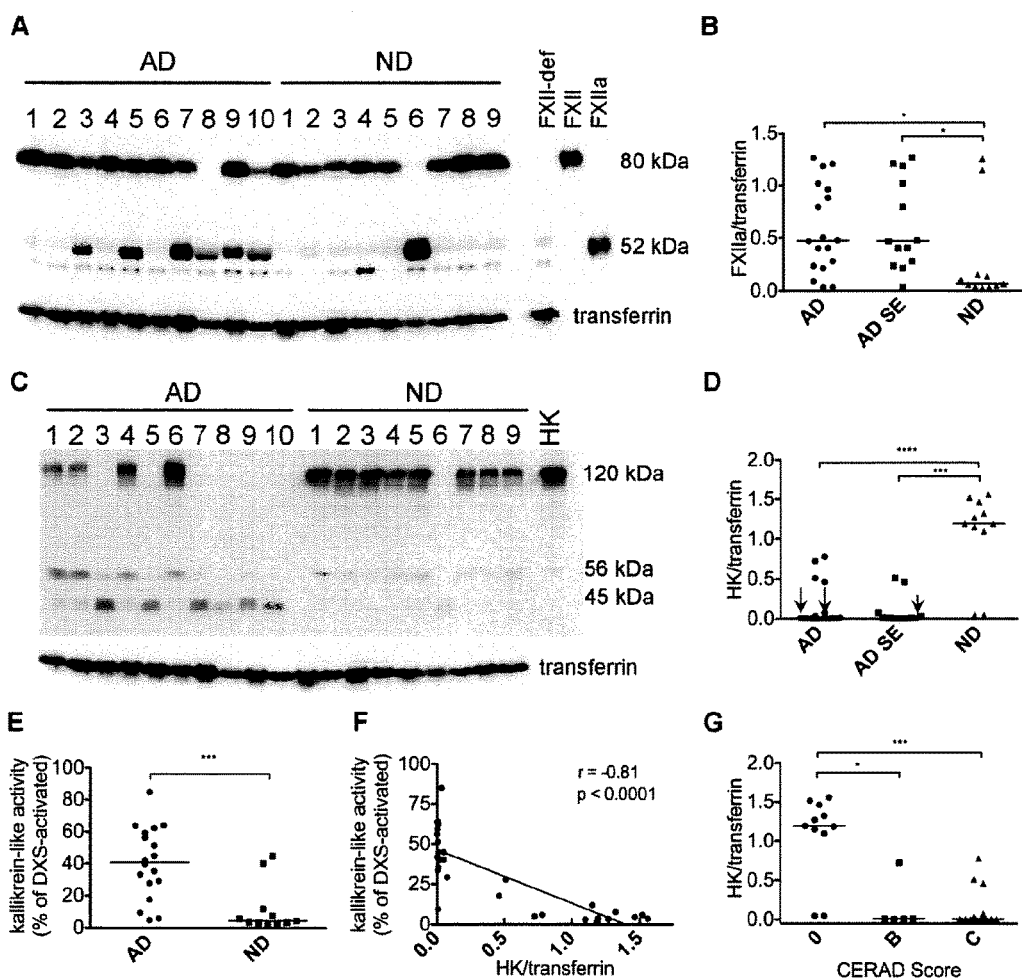
FIG. 1. Activation of the FXIIa-driven contact system in AD patient plasma from Group 1. (A) Western blot analysis of FXIIa and transferrin loading control in plasma of 18 AD patients and 11 ND controls from Group 1 (representative samples shown) showing FXII zymogen (80 kDa) and the FXIIa heavy chain (52 kDa). Lane loaded with FXII-deficient human plasma (FXII-def) shows that the bands just below and above the FXIIa band are non-specific. (B) FXIIa levels normalized to transferrin were significantly higher in AD (p=0.029) than ND plasma. When AD cases with a history of stroke (n=5) were excluded from the analysis, FXIIa levels in AD with stroke-excluded cases (AD SE) remained significantly higher than in ND plasma (p=0.018). (C) Western blot analysis of HK in representative samples showing intact HK (120 kDa), HK light chain (56 kDa), and light chain fragment (45 kDa). Lane labeled "HK" is loaded with purified HK for positive control. (D) Intact HK levels normalized to transferrin were significantly lower in AD (p<0.0001) than ND plasma. When AD cases with a history of stroke (n=5) were excluded from the analysis, intact HK levels in AD with stroke excluded cases (AD SE) remained significantly higher than in ND plasma (p=0.0002). Arrows are for AD and AD SE groups and represent individuals who developed cognitive decline at least one year after blood draw. (E) Kallikrein-like activity was higher in AD plasma compared to ND (p=0.0006). (F) Kallikrein-like activity was inversely correlated to intact HK levels (r=−0.81,p<0.0001). (G) HK levels normalized to transferrin were higher in both individuals with CERAD score B (p=0.003) and CERAD score C (p<0.0001) than in individuals with CERAD score 0. Samples were analyzed 3 separate times with similar results. Results are presented as vertical scatter plots with medians, with statistical significance determined using the Mann-Whitney test for two-group comparisons and the Kruskal-Wallis test with Dunn's Multiple Comparison posttest for comparisons between multiple groups.
Figure 25:
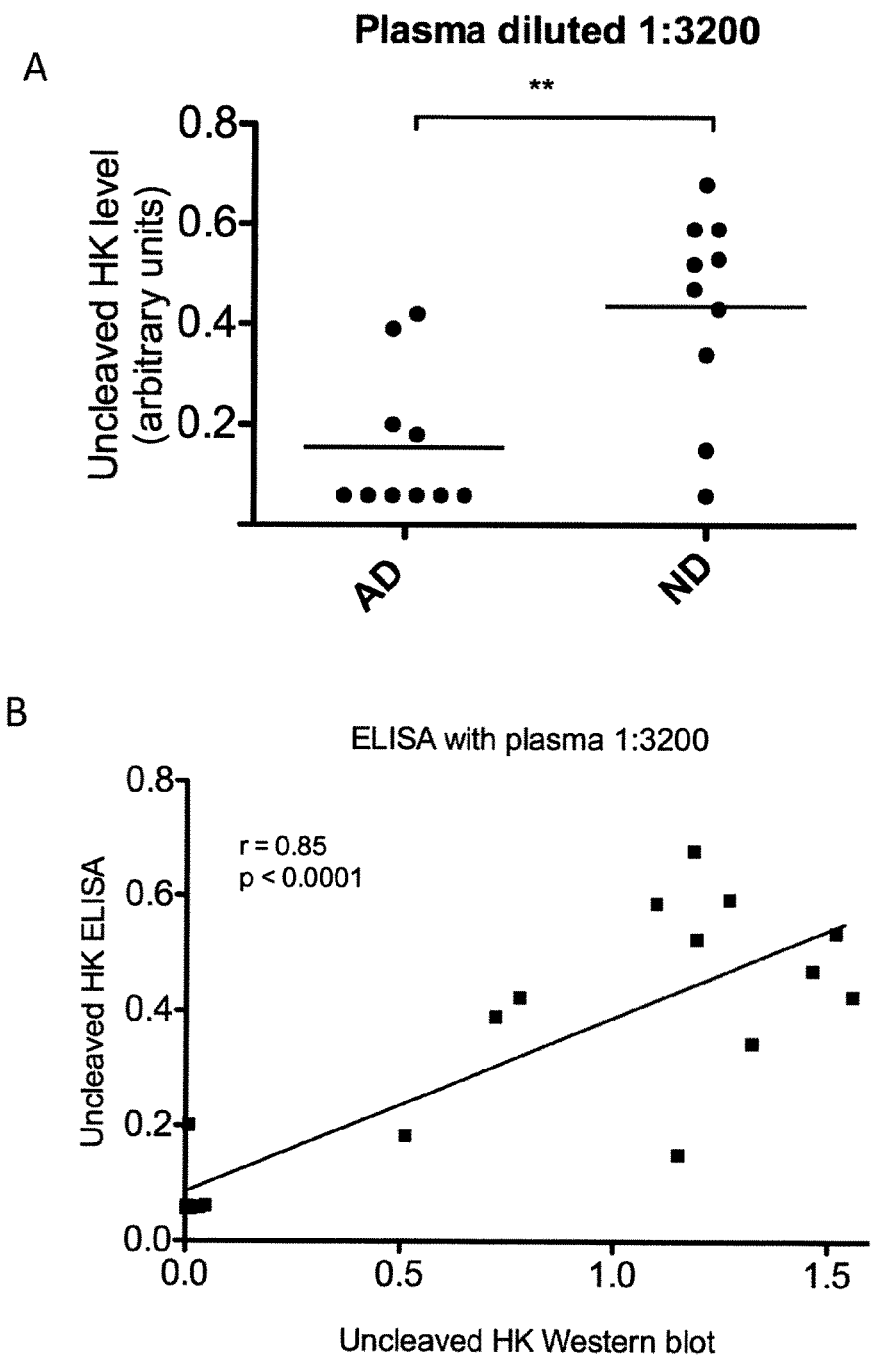

FIG. 25. Intact HK (also referred to herein as "HK") ELISA in AD patient and ND control plasma from Group 1 as described in the accompanying Example. (A) Plasma samples from 10 AD patients and 10 ND controls from Group 1 diluted 1:3200 were analyzed by our sandwich ELISA for intact HK. Levels of intact HK were decreased in AD plasma compared to ND plasma (p=0.002). (B) Levels of intact HK detected by ELISA in (A) correlated with levels of intact HK detected by Western blot in FIG. 1C,D (r=0.85, p<0.0001).

Figure 26:
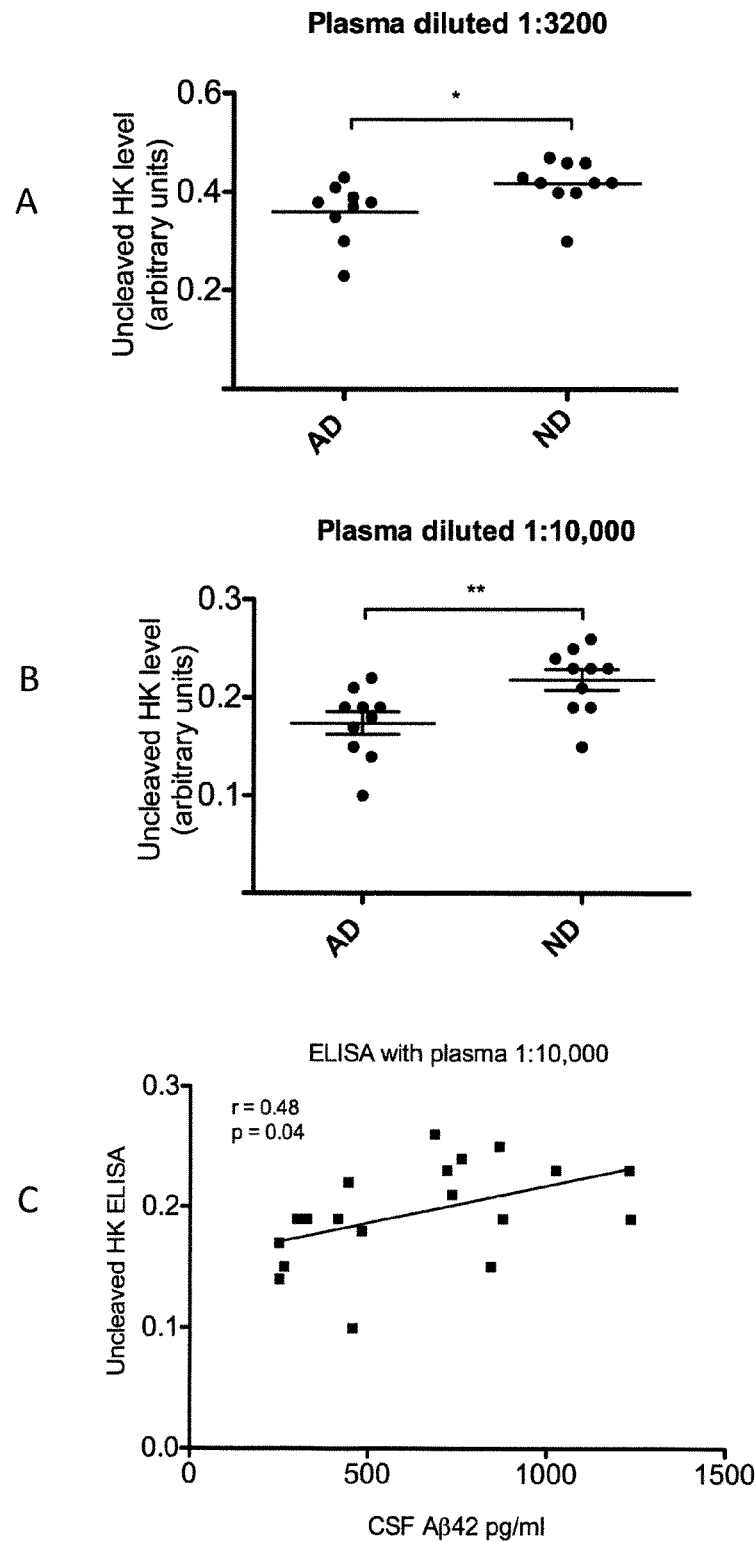

FIG. 26. Intact HK ELISA in AD patient and ND control plasma from Group 2. (A) Plasma samples from 10 AD patients and 10 ND controls from Group 2 diluted 1:3200 were analyzed by our sandwich ELISA for intact HK. Levels of intact HK were decreased in AD plasma compared to ND plasma (p=0.03). (B) Plasma samples from 10 AD patients and 10 ND controls from Group 2 diluted 1:10,000 were analyzed by our sandwich ELISA for intact HK. Levels of intact HK were decreased in AD plasma compared to ND plasma (p=0.007). (C) Levels of intact HK detected by ELISA in (B) correlated with levels of CSF Aβ42 (r=0.48, p=0.04).

FIG. 27. Schematic showing pre-clearing samples of intact HK to detect HKc.

DETAILED DESCRIPTION

There is strong genetic and experimental evidence that the Aβ peptide is a primary driver of both early onset and sporadic AD. The direct neuronal toxicity of Aβ in vitro is well documented, but the mechanism by which Aβ disrupts neuronal function in AD patients is still unclear. In the present disclosure we demonstrate that Aβ can activate factor XII (FXII) in purified protein systems, human plasma, and mouse plasma, and that Aβ-mediated activation of FXII initiates both the blood clotting cascade and inflammatory processes. These systems, when inappropriately stimulated, could lead to the neuronal death and cognitive decline characteristic of AD.

In more detail, it is unlikely that direct toxicity of Aβ to neurons is the sole factor responsible for eliciting AD. Indeed, inflammation is a well-established component of AD pathology, and although it is still not known whether inflammation drives pathology or is the result of other disease processes, it likely contributes to neuronal damage and cognitive decline in AD (Wyss-Coray and Rogers, 2012). Furthermore, the cerebral vasculature in the AD brain is abnormal, and conditions associated with vascular disease states like diabetes, hypertension, hypercholesterolemia, metabolic syndrome, atrial fibrillation, and Factor V Leiden are all associated with increased risk of AD (Humpel, 2011). In keeping with a possible link between AD and vascular dysfunction, epidemiological and experimental data suggest the existence of a prothrombotic state in AD patients and mouse models (Cortes-Canteli et al., 2012). The role of a prothrombotic state in AD is supported by improvements in AD pathology and memory in AD patients (Ratner et al., 1972; Walsh, 1996; Walsh et al., 1978) and mice (Bergamaschini et al., 2004; Timmer et al., 2010) following treatment with anticoagulants.

If the inflammatory and prothrombotic states observed in AD have a causative role in neuronal dysfunction, agents capable of triggering these states are of particular interest to disease etiology. Without intending to be constrained by any particular theory, we found the notion that that Aβ could act as such a trigger by interacting with plasma FXII to be attractive. The active form of FXII (FXIIa) activates the plasma contact system, launching both prothrombotic and proinflammatory pathways (Rennéet al., 2012). FXIIa activation of factor XI (FXI) in the intrinsic coagulation cascade leads to thrombin generation and fibrin formation, whereas FXIIa activation of plasma prekallikrein (PPK) to plasma kallikrein (PK) leads to the release of bradykinin from its precursor HK. Bradykinin can trigger inflammatory processes including blood brain barrier permeability, vasodilation, and edema formation (Leeb-Lundberg et al., 2005).

In this disclosure we demonstrate that Aβ42 oligomers trigger activation of both the FXIIa-mediated intrinsic coagulation pathway, promoting thrombin generation, and as noted briefly above, the FXIIa-mediated kallikrein-kinin pathway, leading to HK cleavage. Moreover, we show for the first time that there are higher plasma levels of FXIIa and increased HK cleavage in AD patient plasma compared to non-demented control plasma. Thus, the results presented in this disclosure indicate that the Aβ-mediated activation of FXII and subsequent cleavage of HK observed in vitro also occurs in AD patient plasmas. This result is in contrast to previous work which showed that the activation state of HK in AD patient plasma did not differ from control plasma (Bergamaschini et al., 2001).

In embodiments, this disclosure includes determining Aβ-mediated activation of FXII for diagnosis, or to aid in the diagnosis of AD. In embodiments, determining Aβ-mediated activation of FXII comprises determining an amount of cleaved HK (HKc), HK, and/or a ratio of HKc to HK. Cleaved HK is also referred to herein from time to time as "HKc" and uncleaved HK is referred to as "high molecular weight HK" or "intact HK." It will be recognized by those skilled in the art from this disclosure that FXII activation is amplified in HK cleavage.

In embodiments, determining HK, HKc and/or a ratio of HKc to HK provides a diagnosis, or aids in a diagnosis of AD. In general, determining an amount of HK that is equivalent to or similar to a normal control aids in a determination that the individual does not or is likely to not have AD, while determining an amount of HK that is less than a normal control aids in a diagnosis that the individual has or is likely to have AD or develop symptoms thereof. Likewise, determining an amount of HKc that is greater than a normal control aids in a diagnosis that the individual does or is likely to have AD, while determining an amount of HKc that is similar to a normal control aids in a diagnosis that the individual does not or is likely to not have AD. In embodiments, the disclosure can further comprise determining one or more other markers such that the risk of false positive diagnosis of AD due to a non-AD condition is mitigated. For instance, in addition to the testing described above, the present disclosure includes but is not necessarily limited to testing for the presence of markers that are positively correlated with other disorders or conditions, such as systemic amyloidosis, hyperlipidemia, ischemic stroke, myocardial infarction, coronary heart disease, acute allergic reactions, hereditary angioedema, teenage systemic lupus patients, rheumatoid arthritis, certain cancers, and combinations thereof. Some of the conditions mentioned above, such as allergic reactions and hereditary angioedema, are acute, and individuals would not be tested for AD during attacks (to avoid false positive AD diagnosis). In other conditions such as systemic lupus and certain cancers, other markers of disease are also present. To further diminish the chance for false positive AD diagnosis, in certain embodiments measurement of plasma HK and HKc levels may be done in conjunction with the determination of other AD markers, such as brain amyloid imaging, CSF Aβ, tau, and phosphorylated tau levels, and measures of cognitive decline.

In one aspect, the present disclosure comprises obtaining and testing any suitable biological sample from an individual who is suspected of having or is at risk for developing AD. In embodiments, the individual from whom the sample is obtained is more than 50 years old. In embodiments, the sample comprises whole blood or plasma. In embodiments, the sample comprises a solid tissue, such as a biopsy or other section of a tissue or organ. In one embodiment, the sample does not include cerebrospinal fluid (CSF). The biological sample can be used directly, or it can be subjected to a processing step before being tested.

The amount of HK, or HKc, or a combination thereof, can be compared to any suitable reference, examples of which include but are not limited to samples obtained from confirmed AD patient plasma, or non-demented control plasma, or a standardized curve(s), and/or experimentally designed controls such as known input HK or HKc used to normalize experimental data for qualitative or quantitative determination of the amount of HK or HKc, or a ratio thereof, or a cutoff value, and to normalize for mass, molarity, concentration and the like. The reference level may also be depicted as an area on a graph. In certain embodiments, determining HK or HKc, or a ratio thereof, facilitates staging the degree and/or severity of AD, and/or can be used to monitor the progress of an AD therapeutic approach, including but not necessarily limited to medicinal, nutritional and behavioral AD therapies designed to improve cognitive function or to slow its deterioration.

In general, aspects of this disclosure include testing samples using immunological-based assays that utilize one or more binding partners that are specific for native intact HK, or are specific for HKc, and can be used alone and in combination with one another, and in combination with other binding partners which recognize other markers if desired. In embodiments, the assays involve use of detectably labeled binding partners to facilitate performance of various immunodiagnostic assays, including but not necessarily limited to immunoabsorbent-based detection methods, such as ELISA assays, and immunohistochemical approaches. In embodiments, the disclosure provides at least two binding partners which can be used in immunological assays to determine HKc and HK. In embodiments, the binding partners are antibodies or antigen-binding fragments thereof.

In order to illustrate embodiments of the invention reference is made to FIGS. 11A and 11B. FIG. 11A depicts uncleaved FIX showing the presence of the bradykinin peptide sequence (BK) at residues 363-371 in a single, intact HK polypeptide having a single N- and C-terminus. FIG. 11B shows cleaved HK (HKc) with liberated BK and a predicted structural rearrangement illustrated by the movement of domain D5 distal to D3, with a concomitant generation of a distinct C-terminus ending in residue 362 in D3. It will be evident that excision of the bradykinin sequence results in a distinct polypeptide comprised of D1-D3, and a distinct polypeptide comprised of D5 and D6, which remain joined to each other by the disulfide bond illustrated by the dotted line. Thus, HK and HKc differ from one another by release of BK and formation of two distinct polypeptides that are covalently linked to one another via a disulfide, which prior to HK cleavage exists as a single polypeptide having an intra-polypeptide disulfide. The graphical depiction of HK in FIG. 11A and HKc in 11B and generation of antibodies and antibody fragments that can bind with specificity to HK, HKc, and both HK and HKc, relates to the following sequences:

signal peptide in SEQ ID NO:1. In certain embodiments, the signal peptide can be numbered −17 through 0 to be consistent with alternative amino acid numbering that is known in the art.

SEQ ID NO:2 is the HK heavy chain (63 kDa) comprising D1, D2 and D3: QESQSEEIDCNDKDLFKAVDAALK-KYNSQNQSNNQFVLYRITEATKTVGSDTFYSFKYE IKEGDCPVQSGKTWQDCEYKDAAKAATGECTATVG-KRSSTKFSVATQTCQITPAEGPV VTAQYDCLGCVH-PISTQSPDLEPILRHGIQYFNNNTQHSSLFML-NEVKRAQRQVVAGLN FRITYSIVQTNCSKENFLFLTPDCKSLWNGDTGECTD-NAYIDIQLRIASFSQNCDIYPGKD FVQPPT-KICVGCPRDIPTNSPELEETLTHTITKLNAENNATFY-FKIDNVKKARVQVVAGK KYFIDFVARETTCSKESNEELTESCETKKLGQSLDC-NAEVYVVPWEKKIYPTVNCQPLG MISLMK (SEQ ID NO:2) In certain embodiments, residues 1-9 are not considered to be part of Domain 1 and thus numbering of amino acids can be adjusted accordingly.

The bradykinin peptide is SEQ ID NO:3: RPPGFSPFR, which is located at positions 363-371 in SEQ ID NO:1 as (SEQ ID NO:1)

MKLITILFLCSRLLLSLTQESQSEEIDCNDKDLFKAVDAALKKYNSQNQSNNQFVLYRIT

EATKTVGSDTFYSFKYEIKEGDCPVQSGKTWQDCEYKDAAKAATGECTATVGKRS

STKFSVATQTCQITPAEGPVVTAQYDCLGCVHPISTQSPDLEPILRHGIQYFNNNTQ

HSSLFMLNEVKRAQRQVVAGLNFRITYSIVQTNCSKENFLFLTPDCKSLWNGDTGE

CTDNAYIDIQLRIASFSQNCDIYPGKDFVQPPTKICVGCPRDIPTNSPELEETLTHTIT

KLNAENNATFYFKIDNVKKARVQVVAGKKYFIDFVARETTCSKESNEELTESCETK

KLGQSLDCNAEVYVVPWEKKIYPTVNCQPLGMISLMKrppgfspfrSSR

IGEIKEETTVSPPHTSMAPAQDEERDSGKEQGHTRRHDWGHEKQRKHNLGHGHKHE

RDQGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPSLAK

PGVTVTFSDFQDSDLIATMMPPISPAPIQSDDDWIPDIQIDPNGLSFNPIS

DFPDTTSPKCPGRPWKSVSEINPTTQMKESYYFDLTDGLS.

Figure 11:
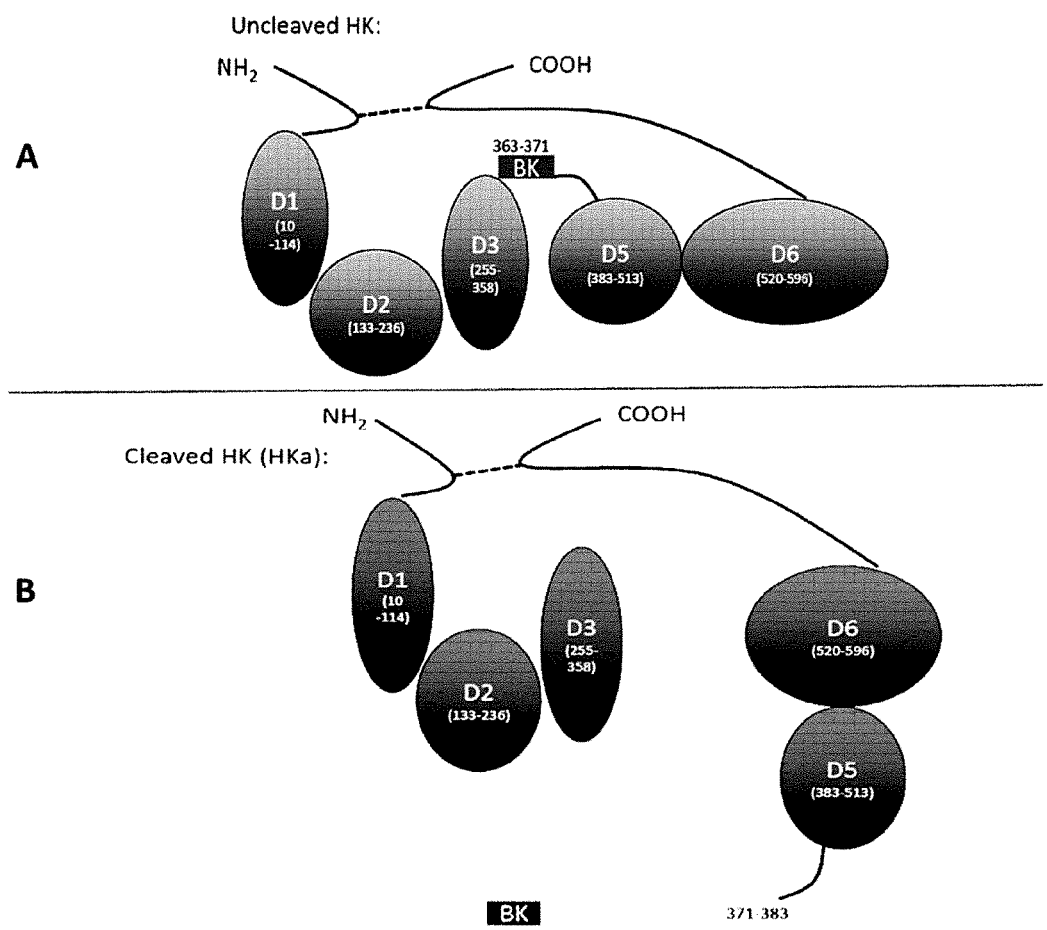
FIG. 11. Graphic representation of HK (FIG. 11A) and HKc (FIG. 11B), domains, disulfide bond, and bradykinin.

SEQ ID NO:1 is the uncleaved (120 kDa) human high molecular weight kininogen (HK) amino acid sequence and is depicted in FIG. 11A shown with the 18 amino acid signal peptide at the N-terminus in italics, the heavy chain sequence is shown in bold, the bradykinin sequence is shown in lower case, and the sequences used in part to design synthetic peptides for generating antibodies according to this disclosure underlined and enlarged. The light chain begins with the Ser residue immediately C-terminal to the bradykinin sequence and continues to the C-terminal Ser. It should be noted that the amino acid residue numbering provided in FIG. 11 reflects amino acid numbering that does not include the signal peptide sequence. Thus, for example, bradykinin is numbered as beginning at residue 363 in FIG. 11, but the bradykinin sequence begins at position 381 in SEQ ID NO:1 due to the inclusion of the 18 amino acid signal peptide in SEQ ID NO:1 as numbered without the 18 amino acids of the N-terminal which constitute the signal peptide and are often not included in HK amino acid numbering.

SEQ ID NO:4 is the HK light chain (58 kDa, sometimes assigned 56 kDa) comprising D5 and D6:

(SEQ ID NO: 4)
SSRIGEIKEETTVSPPHTSMAPAQDEERDSGKEQGHTRRHDWGHEKQR

KHNLGHGHKHERDQGHGHQRGHGLGHGHEQQHGLGHGHKFKLDDDLE

HQGGHVLDHGHKHKHGHGHGKHKNKGKKNGKHNGWKTEHLASSSEDST

TPSAQTQEKTEGPTPIPSLAKPGVTVTFSDFQDSDLIATMMPPISPAP

-continued
IQSDDDWIPDIQIDPNGLSFNPISDFPDTTSPKCPGRPWKSVSEINPT

TQMKESYYFDLTDGLS.

SEQ ID NO:5 is an additional cleavage product (45 kDa) that can be detected based on cleavage immediately C-terminal to the K that is shown in bold and underlining in SEQ ID NO:4 above:

(SEQ ID NO: 5)
HNLGHGHKHERDQGHGHQRGHGLGHGHEQQHGLGHGHKFKLDDDLEHQG

GHVLDHGHKHKHGHGHGKHKNKGKKNGKHNGWKTEHLASSSEDSTTPSA

QTQEKTEGPTPIPSLAKPGVTVTFSDFQDSDLIATMMPPISPAPIQSDD

DWIPDIQIDPNGLSFNPISDFPDTTSPKCPGRPWKSVSEINPTTQMKES

YYFDLTDGLS

It will be apparent from the foregoing that uncleaved HK is composed of a heavy chain which contains amino acids 1-362, a bradykinin sequence of amino acids 363-371, and a light chain composed of amino acids 372-626. The cysteines forming the disulfide are Cys10 and Cys596. This amino acid numbering is based on the HK sequence presented in SEQ ID NO:1 wherein the 18-mer N-terminal signal peptide is not included, and thus residue Q at position 19 in SEQ ID NO:1 is assigned position 1, and the other locations are numbered in relation to this Q as the N-terminus. In one embodiment, HKc as described herein comprises the intact HK sequence, but without the bradykinin peptide sequence (SEQ ID NO:3). It will be recognized from this description and as otherwise known in the art, given the benefit of this disclosure, that when HK is cleaved to HKc, the resulting HKc heavy chain acquires a new C-terminus, as shown for the C-terminus of SEQ ID NO:2. The resulting HKc light chain also acquires a new N-terminus, beginning with SSRIGEIKEETTVSP (SEQ ID NO:13) as shown for SEQ ID NO:4. Further cleavage of the HKc light chain may create another N-terminus (HNLGHGHKHERDQGH-GHQRG—SEQ ID NO:14).

The present disclosure encompasses generating antibodies that in one aspect bind with specificity to HK, and in another aspect bind with specificity to HKc. The disclosure also includes generating antibodies that are specific to an epitope that is shared by the HKc and uncleaved HK, and will accordingly be capable of binding all forms of HK, except for the related low molecular weight kininogen (LK). LK is a splice variant of HK. LK and HK share identical heavy chains (SEQ NO:2) and BK peptide (SEQ NO:3). However, the light chains of HK and LK differ dramatically: only amino acids 372-383 are shared. LK also has a unique light chain following shared residues 1-383 which will not be described here. Thus, amino acids 384-626 in SEQ NO:4 are found in HK/HKc and not in LK. Antibodies specific to epitopes found on amino acids 384-626 would therefore bind HK and/or HKc but not LK. The antibodies specific to an epitope that is shared by the HKc and uncleaved HK will be generated by targeting the unique light chain of HK. Specifically, C-terminal regions of the HK light chain (SEQ ID NO: 4) can be used to generate antibodies capable of recognizing both HK and HKa, but not LK.

In general, when reference is made to antibodies that bind with specificity in this disclosure, such reference includes antigen binding fragments thereof, unless otherwise noted. An antibody that binds "with specificity" to or is "specific for" HK can be interpreted to mean that it exhibits no detectable binding to HKc, such as in an ELISA assay, or can have any binding kinetic parameter that is, for example, indicative of an affinity for HKc that is less than 80%, 70%, 60%, 50%, 40%, 30%, 20%, 10%, including all integers there between, relative to its affinity to HK. Likewise, an antibody that binds "with specificity" to HKc can be interpreted to mean that it exhibits no detectable binding to HK, such as in an ELISA assay, or can have any binding kinetic parameter that is, for example, indicative of an affinity for HK that is less than 80%, 70%, 60%, 50%, 40%, 30%, 20%, 10%, including all integers there between, relative to its affinity to HKc. Finally, an antibody that binds "with specificity" to HK and HKc but not to LK can be interpreted to mean that it exhibits no detectable binding to LK, such as in an ELISA assay, or can have any binding kinetic parameter that is, for example, indicative of an affinity for LK that is less than 80%, 70%, 60%, 50%, 40%, 30%, 20%, 10%, including all integers there between, relative to its affinity to HK and HKc. Such binding parameters are known to those skilled in the art, and include but are not necessarily limited to measuring $K_D$, i.e., the equilibrium dissociation constant between the antibody and its antigen, and can be analyzed using any antigen binding/affinity kinetic parameters. Many methods for measuring antibody affinity for an antigen or a specific epitope(s) are known and include but are not necessarily limited to microfluidic based approaches, surface plasmon resonance, total internal reflection ellipsometry, analysis using the process that is commercially available under the trade name BIACORE, and others.

Thus, and without intending to be constrained by any particular theory, in embodiments, the present disclosure provides antibodies that bind with specificity to HK as it is illustrated in FIG. 11A, and antibodies that bind with specificity to HKc, as it is illustrated in FIG. 11B, and antibodies that will bind with specificity to HK and HKc. The present disclosure accordingly includes making and using an HKc specific antibody that will be specific for at least one epitope that is likely inaccessible to the antibody prior to cleavage of HK. Likewise, the present disclosure includes making and using an HK specific antibody that will recognize an epitope that is unique in HK due to its uncleaved form. As discussed above, the disclosure also includes making and using an antibody that binds with specificity to an epitope that is shared by the HKc and HK, and will accordingly be capable of binding all forms of HK, but not LK. This disclosure includes any of the antibodies described herein, where the antibodies are directed to a linear or conformational epitope. Further, any of the antibodies can have any Ig subtype. In one embodiment, the antibodies are IgG antibodies.

In an illustrative approach, the disclosure includes an immunodetection based diagnostic, such as an ELISA assay, which includes use of a first antibody that binds with specificity to both HK and HKc (but not to LK) and a second antibody that binds with specificity to HKc, or a second antibody that binds with specificity to HK. In embodiments the first antibody is a capture antibody and the second antibody is a detection antibody as those terms are used by the skilled artisan to conventionally refer to antibody pairs that are used in ELISA assays. Thus, for detection of HKc in human plasma in an ELISA assay, the disclosure includes use of a capture antibody that is specific for both HK and HKc (but not LK) immobilized on the ELISA plate, and a detection antibody that is specific for only HKc. Likewise, for the detection of HK in human plasma, the disclosure includes use of a capture antibody that is specific for both HK and HKc (but not LK) immobilized on the ELISA plate, and a detection antibody that is specific for only HK. Given the benefit of this disclosure these configurations can be readily adapted for use in direct ELISA, or sandwich ELISA, or any other immunodiagnostic assays.

In order to develop antibodies that are specific for HK, or for HKc, or for both HK and HKc, the peptides summarized in the following Table 1 are used in immunization protocols using standard techniques and as further described below. Immunization strategies using full-length HK and HKc are also included in this disclosure.

TABLE 1

| Peptide ID | Amino acid sequence | Position in HK (includes signal peptide) | Antibody Catagory |
|---|---|---|---|
| A | IQSDDDWIPDIQIDPNGLSC (SEQ ID NO: 6) | 581-599 | i |
| B | CPGRPWKSVSEINPTTQMKES (SEQ ID NO: 7) | 614-633 | i |
| C | CNAEVYVVPWEKKIYPTVN (SEQ ID NO: 8) | 351-369 | ii |
| D | CQPLGMISLMK (SEQ ID NO: 9) | 370-380 | ii |
| E | SSRIGEIKEETTVSPC (SEQ ID NO: 10) | 390-404 | ii |
| F | HGHKHERDQGHGHQRGC (SEQ ID NO: 11) | 443-458 | ii |
| G | KKNGKHNGWKTEHLAC (SEQ ID NO: 12) | 511-525 | ii |

In Table 1, peptides in Antibody Category i) (the peptides labeled A and B) are designed to produce a capture antibody that will bind to and immobilize both HK and HKc. These antibodies are directed to the C-terminus of the light chain (SEQ ID NO:4). Peptides in Category ii) (the peptides labeled C-G) are designed to produce antibodies capable of discriminating between native HK and HKc by exhibiting specificity for HKc. Cysteines in peptides B, C, and D are part of the human HK sequence, while cysteines in peptides A, E, F, and G are engineered into the sequence. Thus, the present disclosure includes antibodies and antigen binding fragments thereof that bind with specificity to a peptide selected from the group of peptides whose amino acid sequences comprise or consist of SEQ ID NO:1, SEQ ID NO:2, SEQ SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12. Combinations of such antibodies and antigen binding fragments thereof are also included in this disclosure. Any of these antibodies can be used as a capture antibody or a detection antibody in an immunodetection assay such as an ELISA. Combinations of distinct immunodetection assays for use in diagnosis or to aid in the diagnosis of AD are also included.

In embodiments, use of the antibody as either a capture antibody or a detection antibody is dictated by whether the object of the assay is to detect HKc only, or HK only. In one embodiment, the disclosure includes capture with an HK and HKc recognizing antibody and detecting with a discriminating antibody. In one non-limiting embodiment, a capture antibody or antigen binding fragment thereof suitable for use in an ELISA assay will bind with specificity to an epitope present in a molecule comprised of a distinct HK heavy chain polypeptide and distinct HK light chain polypeptide, wherein the heavy and light chains are covalently linked by disulfide bond, such as a disulfide bond between Cys10 and Cys596, and wherein such molecule does not include the bradykinin sequence. Such an antibody will have specificity for this molecule, but will not have specificity for a contiguous HK polypeptide that comprises the bradykinin sequence. In embodiments, the disclosure includes determining intact HK, whicm may include determining intact HK only, such embodiments being apparent based on this disclosure, and for example, from FIGS. 23-26.

Methods for preparation of antibodies are well-known in the art and can be adapted to produce antibodies with the specificities described herein given the benefit of the present disclosure. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

In one approach, to make a monoclonal antibody, a polypeptide described herein is introduced into a laboratory animal, such as a mouse or other rodent, such as a hamster, over a series of administrations over a period of time spanning several weeks. In embodiments, the polypeptides are modified to include, for example, a non-naturally occurring amino acid, such as a Cysteine as described in Table A, and can further be provided in combination with a carrier protein, such as by being present in a fusion protein or being otherwise covalently linked to a carrier protein. Any suitable carrier protein can be used. In an embodiment, the peptides are conjugated to Keyhole limpet hemocyanin (KLH), which is widely used as a carrier protein for to make immunogens more immunogenic than if provided without the carrier. In making monoclonal antibodies, splenocytes are isolated from the mouse spleen, and isolated B cells are obtained and fused with myeloma cells which have been immortalized using any suitable approach, such as electrofusion. The myeloma cells characteristically lack the hypoxanthine-guanine phosphoribosyltransferase (HGPRT) gene and as a result are sensitive to HAT medium (hypoxanthine-aminopterin-thymidine medium). The fusions are generally exposed to the HAT medium for a period of time, such as from 10 to 14 days, during which a compound such as aminopterin is used to inhibit nucleotide synthesis, resulting in death of unfused cells and survivial of B cell-myeloma hybrids (hybridomas) which have been immortalized and which produce antibodies. The cells are diluted to isolate single hybridomas in single wells of, for instance, a multiwell plate. The hybridomas are then screened to identify those which produce antibodies that specifically recognize the HK, or HKa, or both HK and HKa. Once suitable hybridomas are isolated, the DNA encoding the immunoglobulin (Ig) they secrete can be sequenced, and thus the amino acid sequence of the Ig can be determined, and the complementarity determining regions (CDRs) of the Ig heavy and light chains can be determined and used to make synthetic versions of the antibodies made by the hybridomas, or to make antigen binding fragments of them. Alternatively, the cell that produces the antibody can be cloned to produce identical daughter clones which will provide an ongoing source of monoclonal antibodies.

In another embodiment, the disclosure includes an antigen-binding or variable region fragments, or regions that include only the CDRs, of an antibody descried herein. Examples of suitable antibody fragments include Fab, Fab', F(ab')2 and Fv fragments. Various techniques have been developed for the production of antibody fragments. Traditionally, these fragments were derived via proteolytic digestion of intact antibodies. However, these fragments can now be produced directly by recombinant host cells once the amino acid sequences of the antibodies and/or the nucleotide sequences encoding them are determined. In certain aspects, the fragments of antibodies that are specific for HK, or for HKc, or for HK and HKc, include but are not necessarily limited to Fab, Fab', (Fab')2, Fv, single chain (ScFv), diabodies, multi-valent antibodies, fusion proteins comprising one or more antibody portions, and any other modified immunoglobulin molecule that comprises an antigen recognition site of desired specificity as described herein.

In embodiments, the antibodies and antigen binding fragments of them will specifically recognize at least one epitope present in at least 4 contiguous amino acids of any of the amino acid sequences presented in this disclosure. In embodiments, the epitope has at least 4, 5, 6, or 7 such contiguous amino acids. The epitope can be also be defined by longer sequences, such as up to 20 amino acids as the case may be for any particular immunizing peptide. The disclosure includes structures that have at least one paratope that recognizes at least one of the peptides described herein, or at least two paratopes that recognize at least one of those peptides.

In particular embodiments, disclosure encompasses particular antibodies produced by distinct hybridomas, as further described in Example 13. In an embodiment the disclosure includes the hybridoma referred to as "3E8." The 3E8 mAb binds with specificity to both HK and HKc. 3E8 can be used in a variety of immunological detection assays to separate HK and HKc from, for example, a biological fluid. In embodiments, 3E8 can be used as a capture antibody in, for example, an ELISA assay. The 3E8 mAb was obtained by immunization of hamsters using the peptide corresponding to residues 563-581 (without the signal peptide) of human high molecular weight kininogen (IQSDDDWIPDIQIDPNGLSC—SEQ ID NO:6). The terminal cysteine is added to the native sequence for coupling. Thus, in an embodiment, the disclosure includes a mAb that binds with specificity to a peptide consisting of the sequence of SEQ ID NO:6. Likewise, the disclosure provides a mAb that binds with specificity to both HK and HKc. The disclosure also includes mAb and hybridoma 2B7, which binds with specificity to HK only, and therefore does not bind with specificity to HKc. To obtain 2B7, purified full length human HK and HKc were injected into hamsters and hybridomas were produced and screened to identify those producing mAbs that recognize HK but not HKc in solution.

In other examples, the disclosure includes hybridomas and mAbs produced by them which are termed 6A6-B, 12E5-A, and 15D9. Each of these bind with specificity to HK and HKc. Thus, they are suitable for using, for example, as detection antibodies for total HK measurements, and for detection of HKc following clearance of samples with, for example, 2B7. A non-limiting and representative ELISA assay schematic using mAbs of this disclosure is shown in FIG. 21. A non-limiting and representative combined ELISA/clearance schematic using mAbs of this disclosure is shown in FIG. 27.

In embodiments, any of the antibodies and antigen binding fragments thereof can be detectably labeled, such as with a radioactive or fluorescent tag. Alternatively, the antibodies or antigen binding fragments thereof can be conjugated to an enzyme which can modify a substrate to produce a detectable signal. In embodiments, the intensity of signal produced when the substrate is added will by directly proportional to the amount of HK or HKa in the assay. Suitable enzyme/substrate combinations can be configured to use fluorescent, chemiluminescent or chromogenic substrates. Thus the disclosure includes modifications of the antibodies and antigen binding fragments thereof so that they are coupled to enzymes, or are provided as fusion proteins with other polypeptide sequences. In embodiments, the disclosure includes forming and/or detecting a complex of an antibody and/or antigen binding fragment of it and HK, or HKc, wherein the antibody and/or antigen binding fragment of has been modified, such as being covalently attached to a substrate.

The present disclosure includes polynucleotides encoding the antibodies and antigen binding fragments thereof, expression vectors comprising those polynucleotides, in vitro cell cultures wherein the cells comprise the expression vectors and express the antibodies or the antigen binding fragments thereof, and methods of using such expression vectors and cell cultures for making the antibodies and antigen binding fragments thereof. In an embodiment, the disclosure includes providing a cell culture comprising cells which contain an expression vector encoding an antibody or antigen binding fragment thereof, allowing expression of the expression vector, and separating antibodies or antigen binding fragments thereof from the cell culture.

The present disclosure also provides articles of manufacture, including but not necessarily limited to kits. In embodiments, the articles of manufacture contain one or more antibodies or antigen binding fragments described herein provided in one or more sealed containers, one non-limiting example of which is a sealable glass or plastic vial. The antibodies or antigen binding fragments may be unlabeled, or detectably labeled. The articles of manufacture can include any suitable packaging material, such as a box or envelope or tube to hold the containers. The packaging can include printed material, such as on the packaging or containers themselves, or on a label, or on a paper insert. The printed material can provide a description of using the antibodies and antigen binding fragments thereof in an assay described herein for the purpose of diagnosing AD, or aiding in the diagnosis of AD, or for determining the amounts of HK and/or HKc in a sample, or a ratio of HK to HKc. The articles can also include, for example, reagents for performing an immunodetection assay. Non-limiting examples of such reagents include one or more buffers, such as buffers that are suitable for diluting plasma, and/or for performing steps of an immunodetection assay. In embodiments, the article comprises a kit which includes a buffer for diluting human plasma, such as a buffered saline solution, one example of which is phosphate buffered saline (PBS). The kit may also include a blocking buffer, such as PBS+0.1% Tween-20+1% BSA+0.02% NaN3, and may further comprise a wash buffer, such as Phosphate Buffered Saline Tween-20 (PBS-T), and a reaction stop solution, such as an acid solution, and any suitable diluent solutions for performing an immunodetection assay. Antibody detection reagents may also be included, including but not necessarily limited to enzymes, enzyme substrates, and various conjugates thereof, for producing detectable signal, all of which are well known to those skilled in the art and include but are not necessarily limited to avidin, streptavidin, biotin, phosphatases, peroxidases, fluorescein, such as FITC, and fluorogenic sensors, etc. may be included. Isotype antibody controls can also be included.

In embodiments, a result based on a determination of HK and HKc can be fixed in a tangible medium of expression, such as a digital file saved on a portable memory device, or on a hard drive. The determination can be communicated to a health care provider for aiding in the diagnosis of AD, or for monitoring or modifying a therapeutic or prophylactic approach aimed at reducing the severity or symptoms or AD. In embodiments the disclosure comprises providing a diagnosis of AD and subsequently administering a drug to the individual to alleviate one or more sign or symptom of AD. In embodiments, the disclosure comprises selecting a patient to receive an drug intended to alleviate AD based on the result of an assay described herein, and/or administering to the individual such a drug based on receiving the result of such as assay.

The following specific examples are provided to illustrate the invention, but are not intended to be limiting in any way.

Example 1

The following Examples 1-6 demonstrate, among other features, increased plasma levels of FXIIa, HK cleavage, and kallikrein activity in AD patient plasma compared to non-demented (ND) control plasma. Furthermore, the results show that plasma HK cleavage is increased in a mouse model of AD and in wild type mice intravenously injected with Aβ42, supporting a role for Aβ42 in AD-associated activation of the contact system. Activation of the contact system and associated bradykinin release in AD circulation could contribute to the inflammatory and vascular dysfunction observed in the disease. The data support the use of measuring plasma HK cleavage as a minimally invasive biomarker for identifying AD patients who could benefit from therapeutic strategies directed against FXII.

AD and Control Subject Characteristics.

Two sets of AD patient and non-demented control (ND) plasmas were obtained from two AD tissue banks (see the Example describing materials and methods used for this example). Group 1 consisted of 18 AD and 11 ND samples matched with respect to age and gender (Table 2), and Group 2 consisted of 10 AD and 10 ND samples matched with respect to age (Table 3). The extent of dementia in these individuals had been reported using Clinical Dementia Rating (CDR) scores, where 0=no dementia and 3=severe dementia (Morris J C (1993). Neurology 43(11):2412-2414), as well as Mini Mental State Examination (MMSE) scores, where 30=no dementia and 0=severe dementia (Folstein M F, et al. (1975) Journal of psychiatric research 12(3):189-198). At the time of blood draw, AD cases in Group 1 had an average CDR score of 1.6±1.3 (range 0-3) and an average MMSE score of 16.5±9.6 (range 0-30), corresponding to moderate dementia. The presence of CDR 0 and MMSE 30 individuals in this group can be attributed to the fact that several (n=3) were diagnosed with MCI or AD after blood draw. Upon autopsy, the majority of AD cases in Group 1 (77.8%) were Braak stage 5 or 6, corresponding to severe dementia (Table 2) (Hyman B T (1998) Arch Neurol 55(9): 1174-1176). AD cases in Group 2 had an average CDR score of 1.0±0.6 at the time of blood draw, with the majority (80%) being CDR 0.5 or 1 (Table 3), corresponding to very mild to mild dementia (Morris J C (1993). Neurology 43(11):2412-2414). Group 2 individuals are still living at the time this application or patent was filed and therefore Braak stages are not available.

TABLE 2

Characteristics of AD and ND cases from Group 1

|  | AD (18) | ND (11) |
|---|---|---|
| Gender (% Male) | 61 | 64 |
| Mean age at blood draw (years; SD) | 82.4 (9.1) | 82.5 (6.3) |
| Mean CDR at blood draw (score; SD) | 1.56 (1.28) | 0 (0.2) |
| Mean MMSE at blood draw (score; SD) | 16.5 (9.6) | 28.5 (1.5) |
| CERAD (%) | | |
| None | 0 | 100 |
| B | 27.8 | 0 |
| C | 72.2 | 0 |
| Braak stage (%) | | |
| 0-2 | 16.7 | 100 |
| 3-4 | 5.6 | 0 |
| 5-6 | 77.8 | 0 |
| History of (%) | | |
| Hypertension | 50 | 63.6 |
| Atrial Fibrillation | 5.6 | 18.2 |
| Stroke | 27.8 | 0 |
| Diabetes | 5.6 | 18.2 |
| Hypercholesterolemia | 38.5[#] | 45.5 |
| Myocardial Infarction | 11.1 | 27.3 |

[#]History of hypercholesterolemia data was available for only 13 AD cases.

TABLE 3

Characteristics of AD and ND cases from Group 2

|  | AD (10) | ND (10) |
|---|---|---|
| Gender (% Male) | 30 | 50 |
| Mean age at blood draw (years; SD) | 73.6 (5.8) | 70.5 (3.9) |
| Mean CDR at blood draw (score; SD) | 1.0 (0.6) | 0 (0) |
| CDR (%) | | |
| 0 | 0 | 100 |
| 0.5 | 40 | 0 |
| 1 | 40 | 0 |
| 2 | 20 | 0 |

Example 2

This Example demonstrates that levels of cleaved FXII and HK are increased in AD plasma from Group 1 of Example 1. Plasma was analyzed under reducing conditions, with results reported after normalization to transferrin loading control, plasma levels of which are not altered in AD (16). Cleavage of the FXII zymogen (decreased intensity at 80 kDa) and the corresponding appearance of a FXIIa heavy chain band at 52 kDa were detected in 13 of 18 AD plasmas and 2 of 11 ND plasmas (FIG. 1A). Levels of the 52 kDa heavy chain fragment, the generation of which typically corresponds to FXII activation, were higher in AD than in ND cases (0.47 vs. 0.07, p=0.029; FIG. 1B). Activation of FXII may occur in conjunction with co-morbidities present in AD patients that are absent in controls. However, records of self- or caregiver-reported medical conditions indicate that AD cases did not have higher levels of hypertension, hypercholesterolemia, diabetes, myocardial infarction, or atrial fibrillation than controls (Table 2), arguing against a role for these co-morbidities in the increased FXIIa levels observed in AD patient plasma. Interestingly, history of stroke was found in 5 of 18 (almost 30%) of AD cases, but was absent in ND cases. Stroke is mediated by thrombosis and/or vessel rupture, both of which generate surfaces for FXII activation such as polyphosphates and RNA. However, excluding AD cases with history of stroke did not substantially change the FXIIa levels in AD and ND groups (0.47 vs. 0.07 respectively, p=0.018; FIG. 1B).

The presence of FXIIa in plasma (FIG. 1A) was accompanied by HK cleavage, seen as diminished signal intensity of intact HK bands at 120 kDa (FIG. 1C). AD plasma as a group had much lower levels of intact HK than ND plasma (0.01 vs. 1.19, p<0.0001; FIG. 1D), even when AD cases with history of stroke were excluded (0.01 vs. 1.19, p=0.0002; FIG. 1D). Decreases in intact (single chain) HK levels were accompanied by the appearance of cleaved HK fragments: the cleaved HK light chain band migrating at 56 kDa and an additional 45 kDa band representing a degradation product of 56 kDa cleaved HK light chain. Because HK cleavage products are rapidly degraded (Renné T (2013) Basic Princeples and Clinical Practice., Vol 6, pp 242-253), samples with high levels of HK cleavage did not necessarily have proportionally higher levels of HK light chain, making quantification of the HK breakdown products uninformative. Interestingly, some samples (e.g. AD1 and AD2) that did not have detectable FXIIa showed evidence of HK cleavage, demonstrating that HK cleavage is a more sensitive indicator of contact activation than FXII activation.

To determine whether the reduction in intact HK levels observed by Western blot is a result of contact system activation, we measured the activity of plasma kallikrein, the enzyme responsible for HK cleavage. Kallikrein-like activity, measured by chromogenic substrate assay, was higher in AD plasma compared to ND (40.9% vs. 4.5% of dextran sulfate 500 kDa (DXS)-activated plasma, p=0.0006; FIG. 1E) and correlated with HK cleavage as detected by Western blot (r=-0.81, p<0.0001; FIG. 1F). Since kallikrein generation is triggered by FXIIa, this result also indicates that FXII cleavage detected by Western blot represents FXII activation.

When levels of intact HK were plotted as a function of Consortium to Establish A Registry for Alzheimer's Disease (CERAD) score (a measure of Aβ3 plaque pathology in the brain on autopsy; 0=normal brain; B=probable AD; C=definite AD (20)), plasma from individuals with a CERAD score of 0 had higher levels of intact HK compared to plasma from individuals with a CERAD score of B (1.19 vs. 0.01, p<0.05) or C (1.19 vs. 0.01, p<0.001) (FIG. 1E). The fact that HK cleavage is apparent in the plasma of individuals with CERAD B and does not increase further in those with CERAD C suggests that FXIIa-driven inflammation begins early in disease progression and is mostly developed by the time individuals reach CERAD B status. The idea that HK cleavage is an early event in AD is also suggested by its presence in plasma from three individuals who were cognitively normal at time of blood draw but went on to develop cognitive impairment (red points in FIG. 1D). Indeed, the presence of pre-clinical AD may explain the FXII activation and HK cleavage observed in two ND samples (FIG. 1B,D).

Example 3

Figure 2:
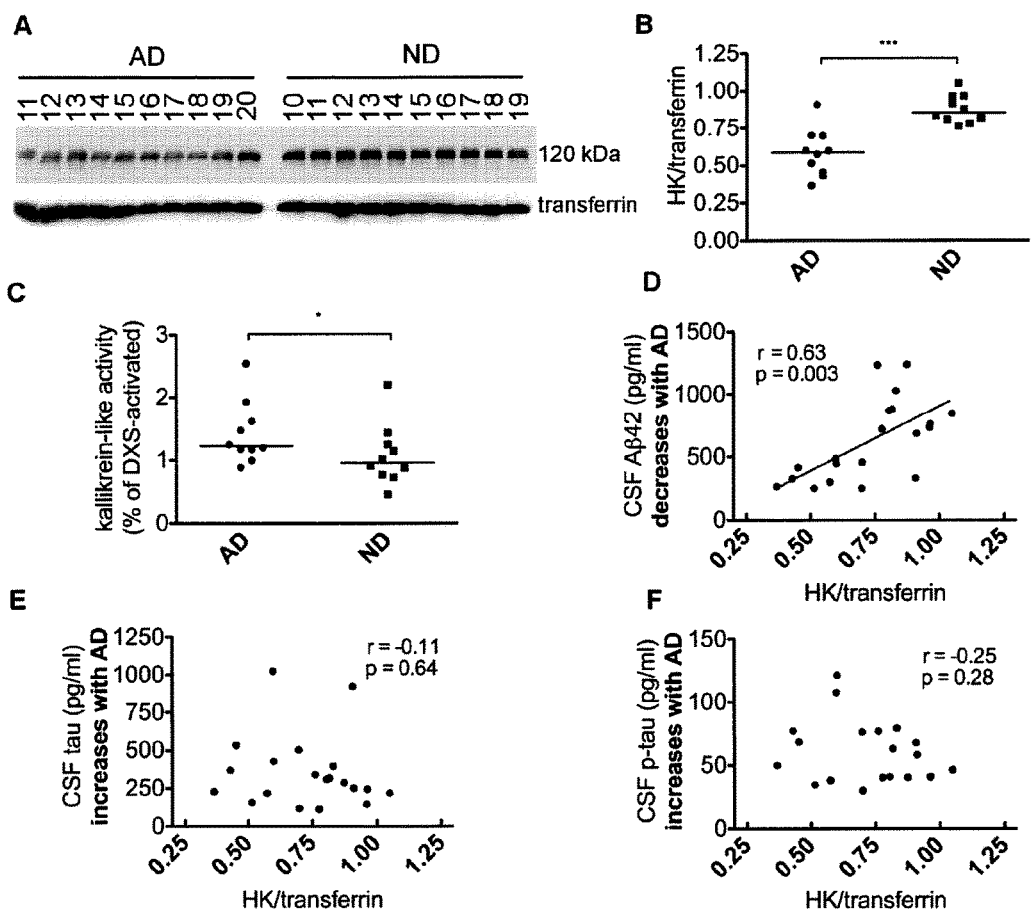
FIG. 2. Activation of the FXIIa-driven contact system in AD patient plasma from Group 2. (A) Western blot analysis of HK and transferrin loading control in plasma of 10 AD patients and 10 ND controls from Group 2. (B) Intact HK levels normalized to transferrin were significantly lower in AD (p<0.0001) compared to ND plasma. (C) Kallikrein-like activity was higher in AD plasma compared to ND (p=0.03). (D) Levels of CSF Aβ42, which decrease with AD, were positively correlated with intact HK levels (r=0.63, p=0.003). (E) Levels of CSF tau, which increase with AD, were not correlated with intact HK levels (r=−0.11, p=0.64). (F) Levels of CSF p-tau, which increase with AD, were not correlated with intact HK levels (r=−0.25, p=0.28). Samples were analyzed 3 separate times with similar results. Results are presented as vertical scatter plots with medians, with statistical significance determined using the Mann-Whitney test.
Figure 5:
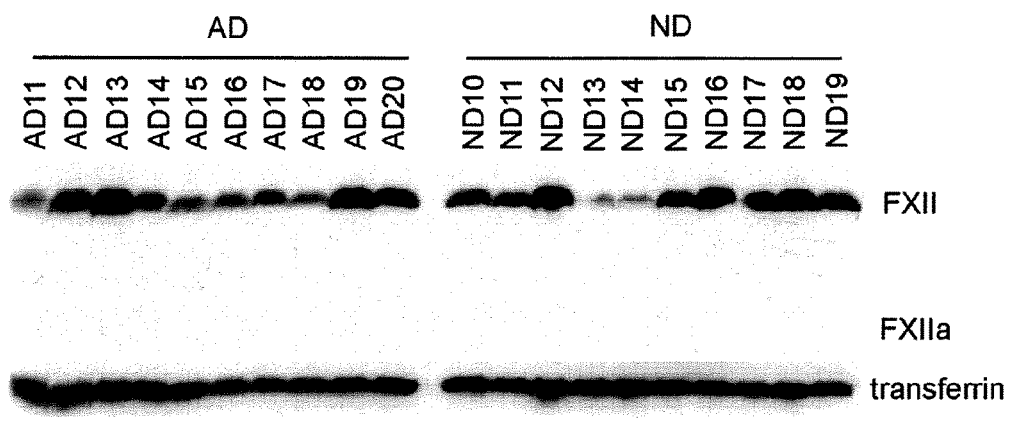
FIG. 5. Western blot analysis of FXII in AD patient plasma. Western blot of plasma samples from Group 2 analyzed with an antibody against FXII and against transferrin as a loading control. No FXIIa heavy chain was detected.

This Example demonstrates that levels of cleaved HK are increased in AD plasma from Group 2 of Example 1. We next tested plasma samples from a different tissue bank and from AD patients at earlier clinical stages of disease (on average). While FXIIa was not detected by Western blot in AD or ND plasma from Group 2 (FIG. 5), intact HK levels were lower in AD than ND (0.59 vs. 0.85; p<0.0001; FIG. 2A,B), as seen in Group 1. Kallikrein-like activity was also increased in AD plasma (1.2% vs. 0.96% of DXS-activated plasma, p=0.03; FIG. 2C), corroborating the decreased levels of intact HK seen by Western blot.

Levels of CSF Aβ42, total tau (tau), and phosphorylated tau (p-tau) in Group 2 were available from the Washington University Alzheimer's Disease Research Center. Decreased CSF Aβ42 levels are thought to be the earliest CSF marker of incipient AD, appearing as early as ~15 years prior to onset of symptoms and remaining low as disease progresses, while CSF tau and p-tau levels (related to neurofibrillary tangle formation and neurodegeneration) begin to rise closer to the appearance of cognitive decline (Musiek E S & Holtzman D M (2012) Current opinion in neurology 25(6): 715-720). We therefore performed correlation analyses for these CSF biomarkers and intact HK levels. Levels of intact plasma HK were positively correlated with CSF Aβ42 (r=0.63; p=0.003; FIG. 2C), consistent with increased HK cleavage in the plasma of individuals with lower CSF Aβ42. Intact plasma HK did not correlate with CSF tau (r=-0.11; p=0.64; FIG. 2D) or p-tau (r=-0.25; p=0.28; FIG. 2E), suggesting that increased HK cleavage may be an early event in AD progression that precedes substantial changes to neuronal injury markers.

Example 4

This Example describes blood draw variables and contact system activation. Undetectable FXIIa and less dramatic HK cleavage in Group 2 than Group 1 may stem from the earlier disease stage of Group 2 cases (CDR score Group 2, 1.0±0.6 vs. Group 1, 1.6±1.3) and from differences in blood collection. While we show that the degree of contact system activation may increase with disease progression (FIG. 2D), the method of blood collection appears to also play a role, since ND plasma in Group 2 had lower kallikrein activity than ND plasma in Group 1 (FIGS. 1E, 2C).

Figure 3:
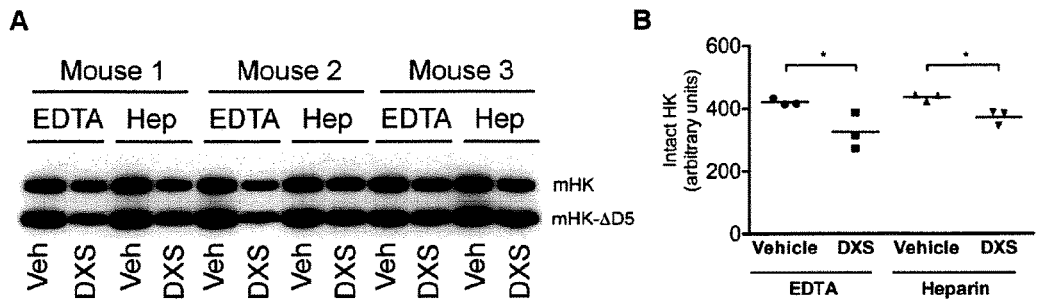
FIG. 3. Blood draw into EDTA or heparin tubes does not affect ex-vivo contact activation. (A) Western blot analysis of WT mouse plasma with an antibody against murine HK (mHK) light chain. Mouse plasma contains mHK (110 kDa) and mHK-ΔD5 (mHK lacking domain 5; 82 kDa) (52). (B) Intact mHK (sum of mHK and mHK-ΔD5 bands) is decreased in samples activated with DXS compared to vehicle in both EDTA and heparin conditions (p<0.05).

In Group 1, blood was drawn into heparinized Vacutainer tubes via vacuum, while Group 2 blood was drawn into EDTA-coated syringes via aspiration. It is known that heparin can promote contact system activation in a purified protein system and in plasma diluted to 30%, but not in plasma diluted to 90%, arguing against heparin-mediated activation of undiluted blood during collection. On the other hand, EDTA is a Zn++ chelator and may therefore prevent ongoing contact activation after blood collection, resulting in detection of less FXIIa and intact HK in Group 2. To test these possibilities, we evaluated the activation potential of blood from wild type C57BL/6 mice collected into heparin or EDTA. Both EDTA- and heparin-anticoagulated plasma treated with the FXII activator dextran sulfate 500 kDa had comparably decreased levels of intact HK (FIG. 3), indicating that heparin-mediated promotion or EDTA-mediated inhibition of ex-vivo FXII activation cannot explain the differences between Groups 1 and 2. However, the possibility remains that long-term storage of frozen plasma with EDTA vs. heparin could lead to differences in ex-vivo contact activation. Another possible explanation is that plasma collected into Vacutainer tubes (with vacuum) has increased FXII-driven thrombin generation and earlier clot formation compared to blood drawn into S-Monovette tubes, which employ a syringe-like mechanism. Thus, blood draw methods used for Group 1 may have resulted in ex-vivo amplification of smaller differences in contact factor activation present in vivo, which did not occur in Group 2.

Example 5

Figure 4:
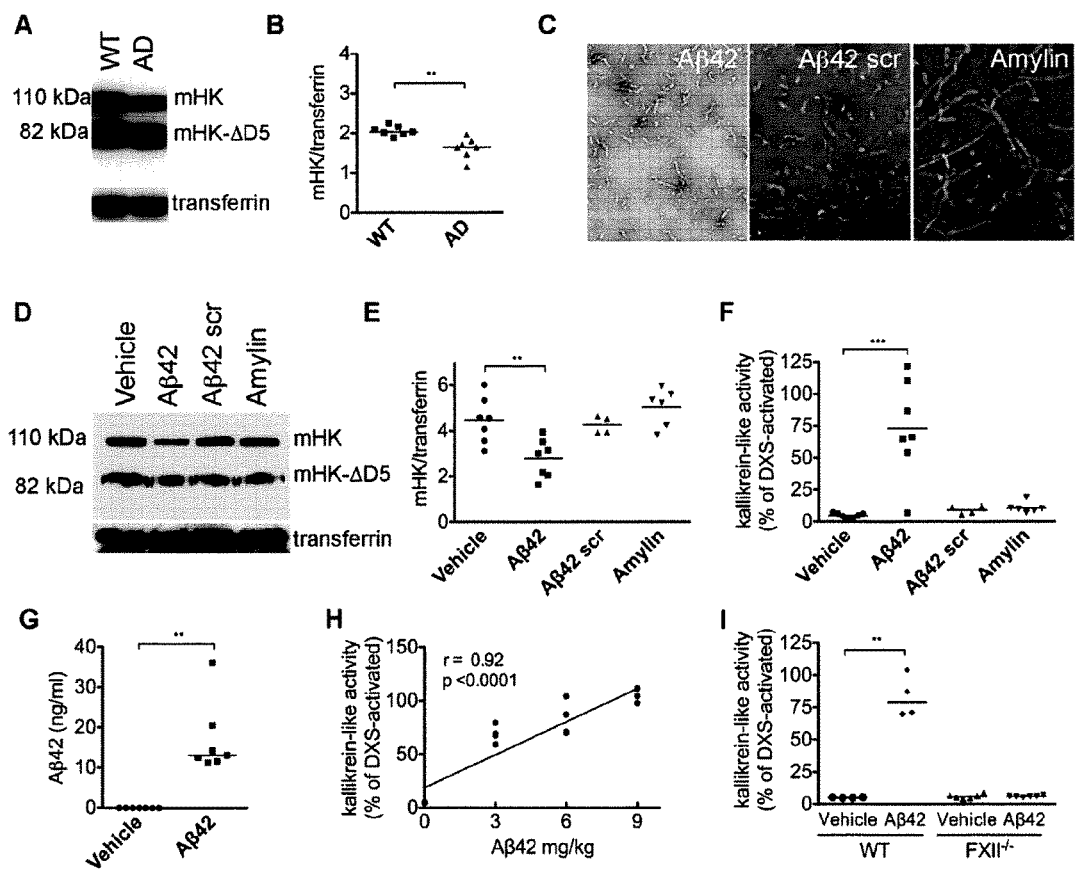
FIG. 4. Activation of the FXIIa-driven contact system in plasma from an AD mouse model and from wild type mice injected with Aβ42. (A) Plasma from AD mice (n=7) and littermate controls (WT; n=7) was analyzed by Western blot with an antibody against mHK light chain. Representative blot showing HK from one AD and one WT mouse (full blot in FIG. 7). (B) The levels of intact mHK (sum of mHK and mHK-ΔD5 bands) normalized to transferrin were lower in AD than WT mice (p=0.0012). (C) Representative TEM images of Aβ42, scrambled (scr) Aβ42, and amylin used for injections. Scale bar=100 nm. (D) Representative blot probed with an antibody against mHK light chain showing C57BL/6 mice injected with either vehicle, Aβ42, Aβ42 scr, or amylin (full blot in FIG. 9). (E) The level of intact HK (sum of mHK and mHK-ΔD5 bands) normalized to transferrin was significantly lower (p<0.001) in mice injected with Aβ42 than in vehicle-, Aβ42 scr-, or amylin-injected mice. (F) Kallikrein activity as measured by chromogenic substrate was increased in plasma from mice injected with Aβ42 but not Aβ42 scr or amylin compared to plasma from mice injected with vehicle (p<0.001). (G) Plasma Aβ42 levels in C57BL/6 mice injected with Aβ42 were significantly higher than in mice injected with vehicle (p=0.001). In mice injected with vehicle, levels of Aβ42 were below the detection limit of the ELISA (0.0156 ng/ml). (H) The dose of Aβ42 (0, 3, 6, or 9 mg/kg Aβ42) injected into WT mice (n=4 per dose) correlated with kallikrein activity levels in plasma (r=0.92, p<0.0001). (I) Kallikrein activity was increased in WT (n=4 per group; p<0.01) but not in FXII−/− mice injected with 6 mg/kg Aβ42 (n=6 per group). Results are presented as vertical scatter plots with medians for panels B, G, and I, and with means for panels E and F, with statistical significance determined using the Mann-Whitney test for panels B and G, ANOVA with Dunnett's post-test for E and F, and Kruskal-Wallis with Dunn's post-test for I.
Figure 6:
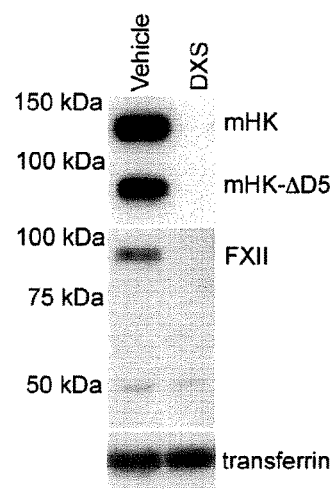
FIG. 6. FXII cleavage in mouse plasma cannot be detected via Western blot. Reducing Western blot with transferrin as a loading control. Plasma from mice injected with dextran sulfate 500 kDa (DXS) has complete cleavage of murine HK (mHK) and murine HK lacking domaing 5 (mHK-ΔD5), while plasma from mice injected with vehicle does not (top panel). While FXII zymogen is completely cleaved, there are no specific bands corresponding to FXIIa fragments (middle panel). Thus, it is not possible to detect increased FXIIa in mouse plasma even following complete FXII activation.
Figure 7:
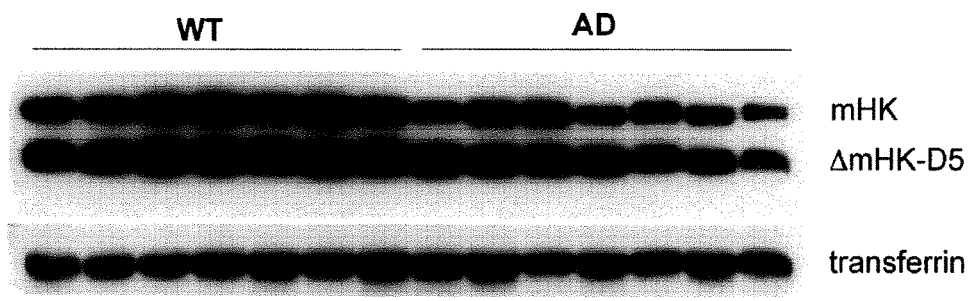
FIG. 7. Full Western blot analysis of HK in AD and WT mouse plasma. Plasma from AD mice (n=7) and littermate controls (WT; n=7) was analyzed by Western blot with an antibody against murine HK (mHK) light chain and transferrin as a loading control.

This Example demonstrates increased contact system activation as seen through decreased levels of intact HK and/or increased kallikrein activity in plasma from a mouse model of AD and in plasma from wild type mice injected with Aβ42. AD patients are a heterogeneous population with various disease etiologies and comorbidities. To analyze FXII activation and HK cleavage in a more homogeneous model, we examined plasma from the Tg6799 mouse model of AD, in which AD pathology is driven by the overexpression of human Aβ (27) (referred to herein from time to time as AD mice). Since detection of FXIIa by Western blot in mouse plasma is technically challenging given the poor ability of antibodies to recognize murine FXIIa fragments (FIG. 6), we focused on HK cleavage as a marker of contact system activation. Compared to non-transgenic wild type littermate controls (WT), AD mice had decreased levels of intact HK (2.0 vs. 1.6, p=0.0012; FIG. 4A,B). These data corroborate HK cleavage in human AD patient plasma and also support the idea that the increased HK cleavage in AD patient plasma is related to Aβ-driven AD pathology and not to comorbidities present in AD patients.

Figure 8:
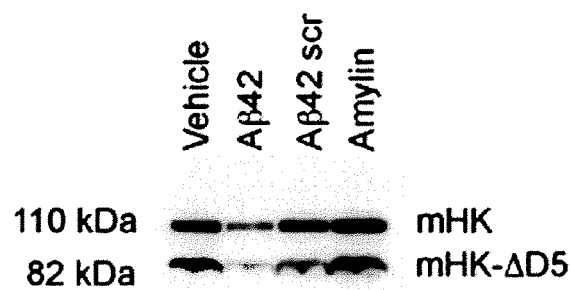
FIG. 8. In vitro activation of WT mouse plasma by Aβ42 and control peptides. C57BL/6 (WT) mouse plasma incubated with Aβ42 but not vehicle, Aβ42 scr, or amylin results in HK cleavage.
Figure 9:
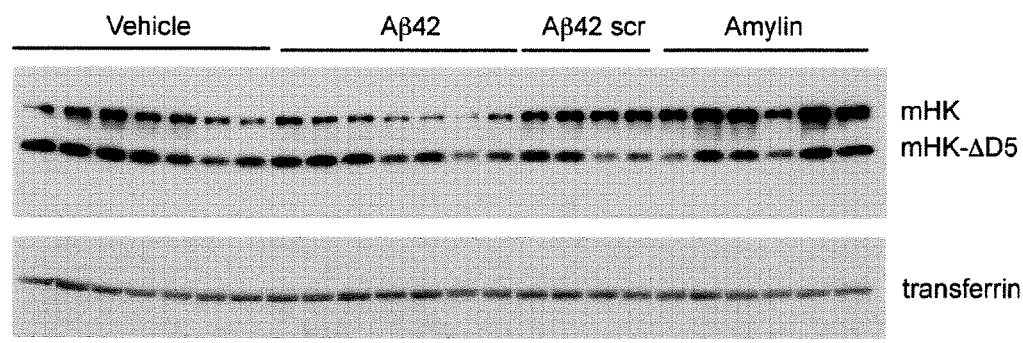
FIG. 9. Full Western blot analysis of HK in WT mouse plasma injected with vehicle, Aβ42, Aβ42 scr, or amylin. Plasma from C57BL/6 (WT) mice injected with vehicle (n=7), Aβ42 (n=7), Aβ42 scr (n=4), or amylin (n=6) was analyzed by Western blot with an antibody against murine HK (mHK) light chain and transferrin.

We next investigated whether the increased HK cleavage found in AD patient and mouse model plasma could be mediated by Aβ42, an aggregation-prone, negatively-charged peptide. To control for non-specific effects, scrambled Aβ42 as well as amylin, another aggregating peptide, were used. Peptide preparations were shown by TEM to be composed of similar sized structures (FIG. 4C). Incubation of Aβ42 but not scrambled Aβ42, amylin, or vehicle with WT (C57BL/6) mouse plasma resulted in HK cleavage ex vivo (FIG. 8), confirming results obtained with human plasma ((Shibayama Y, et al. (1999) Clin Immunol 90(1):89-99); Bergamaschini L, et al. (2001) Neurobiol Aging 22(1):63-69)). C57BL/6 mice were then intravenously injected with the same peptides or vehicle. Plasma from mice injected with Aβ42 but not scrambled Aβ42 or amylin had decreased levels of intact HK (2.8±0.8 vs. 4.5±1.0, p<0.01; FIG. 4D,E) and increased kallikrein-like activity compared to plasma from mice injected with vehicle (73.0±3 8.2% vs. 4.9±1.9% of DXS-activated plasma, p<0.001; FIG. 4F). The presence of Aβ42 in the plasma of injected mice was confirmed by ELISA (17.1±9.0 ng/ml in Aβ42-injected mice compared to undetectable levels in vehicle-injected mice; lower limit of detection=0.0156 ng/ml; FIG. 4G). Aβ42-mediated activation of the contact system in vivo as determined by kallikrein activity in plasma was both dose (r=0.92, p<0.0001; FIG. 4H) and FXII-dependent, since injection of Aβ42 into FXII−/− mice did not result in increased kallikrein activity (FIG. 4I). Our combined results indicate that circulating Aβ42 functions as a FXII contact activator capable of triggering kallikrein activity and HK cleavage in vivo, and support the hypothesis that increased HK cleavage in AD patient and mouse model plasma is due to Aβ42-mediated FXII activation It will be apparent from the foregoing examples that we demonstrate increased activation of the contact system (as determined by FXII activation, kallikrein activity, and HK cleavage) in AD patient plasma, which represents a new potential mechanism of inflammatory pathology in AD. Increased contact system activation is demonstrated in AD mouse models and in human samples from two separate tissue banks.

Example 6

This Example provides a description of materials and methods used to obtain the results described in the foregoing Examples.

Human plasma samples. Experiments with human plasma were approved by the Rockefeller Institutional Review Board. Plasma from AD patients and ND controls was obtained from the University of Kentucky Sanders-Brown Center on Aging (Group 1) and Washington University Knight Alzheimer's Disease Research Center (Group 2). For Group 1, blood from participants giving written, informed consent was drawn into heparinized plastic Vacutainer tubes with a 23 or 21 gauge needle. AD cases were defined by a clinical diagnosis of AD as well as a postmortem Consortium to Establish A Registry for Alzheimer's Disease (CERAD) neuritic plaque score (Mirra et al., 1991, Neurology, 479-486) of B or C, corresponding to probable or definite AD, respectively. ND cases had CERAD scores of 0 and no clinical diagnosis of AD. AD and ND cases were gender and age-matched (Table 2). For Group 2, blood was drawn using EDTA-coated syringes into polypropylene tubes containing a final concentration of 5 mM EDTA. Plasma was prepared by centrifuging blood at 2000×g for 15 min, and flash frozen on dry ice prior to storage at −80° C. AD cases were defined by a Clinical Dementia Rating (CDR) score (Morris, 1993, Neurology, 2412-2414) of ≥0.5 and CSF Aβ42 levels<500 pg/ml, and ND cases were defined by a CDR score of 0 and CSF Aβ42 levels >500 pg/ml (Table 3). CSF Aβ42 cut-off values for AD vs. ND were based on correlations between CSF Aβ42 levels and cortical amyloid load as assessed by positron emission tomography with Pittsburgh Compound B (Fagan et al., 2009, Ann Neurol, 176-183).

Analysis of contact system activation in human plasma by Western blot. Total plasma protein concentration was measured by BCA, and equal amounts of total protein from each sample were analyzed by reducing Western blot with monoclonal antibodies against FXII heavy chain (Haemotologic Technologies), HK light chain (Abcam), and transferrin (Abcam), in that order. Blots were stripped between antibody incubations and developed using Enhanced Chemoluminescent substrate (Perkin Elmer). Protein levels were quantified using densitometric analysis with ImageJ (NIH).

Figure 10:
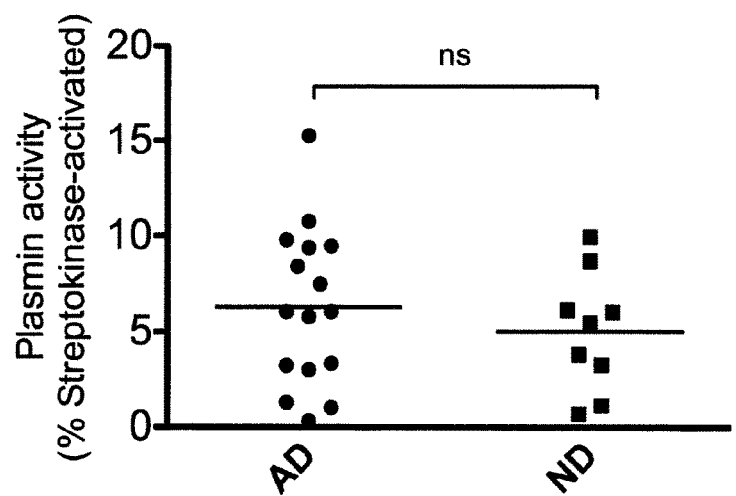
FIG. 10. Plasmin activity does not differ between AD and ND plasma. Plasmin activity in samples from Group 1 was measured by chromogenic substrate Pefa-5329 for plasmin (Pentapharm). Plasma samples diluted 1:30 were mixed with 0.67 mM Pefa-5329 (final concentration) and absorbance read at 405 nm for 30 min. The rate of substrate conversion over time was calculated for each sample and expressed as % of plasmin activity measured in plasma activated with 1 μM streptokinase (Sigma).

Measurement of kallikrein-like activity in human and mouse plasma. Plasma kallikrein-like activity was measured using the chromogenic substrate S-2302 (Chromogenix) based on the method described in Gallimore et al., 1982, Thromb Res, 293-298 with some modifications. Plasma (diluted 1:30) in 20 mM Hepes with 140 mM NaCl was mixed with S-2302 (0.67 mM final concentration) in duplicate, and absorbance at 405 nm was read for 30 minutes at RT in a Molecular Devices Spectramax 384 Plus spectrophotometer. Rate of substrate conversion over time was calculated for each plasma sample by the data acquisition software (Softmax 6.1), and expressed as a percentage of the rate found for normal human or wild type mouse plasma fully activated with dextran sulfate 500 kDa (Sigma). S-2302 can also be cleaved by FXIIa, FXIa, and plasmin. To determine whether S-2302 cleavage was mediated by members of the contact activation pathway (kallikrein, FXIIa, or FXIa) or plasmin, plasmin activity in all samples was determined using a different substrate (Pefachrome-5329, Pentapharm) and found not to differ between AD and ND (FIG. 10).

Mouse lines. The Tg6799 mouse model of AD (Jackson) was used, which is double transgenic for APP/Presenilin 1 and expresses five familial AD mutations: three in APP (K670N/M671L, Swedish; I716V, Florida; V717I, London) and two in Presenilin 1 (M146L, L286V)) under the mouse thy1 promoter. Tg6799 mice develop amyloid plaques at 2 months of age and cognitive impairment by 4-5 months of age. Non-transgenic littermates were used as controls. For Aβ42 injection experiments, 2-month-old C57BL/6 mice (Jackson) and FXII−/− mice backcrossed to C57BL/6 mice for >10 generations were used.

Analysis of contact system activation in AD and wild type mouse plasma. All animal experiments were conducted in accordance with the guidelines of the US National Institutes of Health Guide for the Care and Use of Laboratory Animals and with approval from the Animal Care and Use Committee of The Rockefeller University. Tg6799 mice (n=7) or littermate control mice (WT; n=7) at 6 months of age were anesthetized with atropine (500 mg/kg body weight) and avertin (0.04 mg/kg body weight) intraperitoneally. Blood (100 µl) was collected via retro-orbital bleeding through gel-repel (Sigma) and polybrene (Santa Cruz) coated capillaries into EDTA-coated tubes (BD) containing 5 mM EDTA. Plasma was prepared by centrifugation (1500×g for 15 min, twice), and stored in polypropylene tubes containing 5 mM EDTA. Total protein concentration was determined by BCA, and plasma from each mouse containing 20 µg total protein was analyzed by Western blot using monoclonal antibodies against HK light chain (R&D) and transferrin (Abcam) in that order. Blots were stripped between antibody incubations. Protein levels were quantified by densitometric analysis.

For experiments investigating the effect of different anticoagulants on ex vivo contact system activation, blood from C57BL/6 mice (n=3) was collected into EDTA-coated tubes (as described above) or heparin-coated tubes (Sarstedt). Plasma was prepared as described above, and stored in polypropylene tubes containing an additional 5 mM EDTA (final concentration) or 10 U/ml heparin (final concentration), respectively. Plasma was activated with dextran sulfate 500 kDa (DXS), 0.1 µg/ml final concentration, or vehicle for 20 min at 37° C., reactions stopped with reducing sample buffer, and analyzed by Western blot.

For in vitro and intravenous injection experiments, Aβ42, scrambled Aβ42, and amylin (Anaspec) were prepared as follows: peptides were resuspended in a minimum amount of 1% NH4OH, then diluted to 1 mg/ml with PBS. Peptide concentration was determined by BCA, and the state of aggregation was determined by transmission electron microscopy (see below). Plasma from C57BL/6 mice collected into EDTA as described above was incubated with 20 µM Aβ42, scrambled Aβ42, amylin, or vehicle for 1 hour at 37° C. and analyzed by Western blot. Aβ42 (3, 6, or 9 mg/kg body weight), scrambled Aβ42 (6 mg/kg), amylin (6 mg/kg), or vehicle were administered via retro-orbital injection into 2 month-old C57BL/6 or FXII−/− mice under anesthesia using avertin and atropine as described above. After 6 hours, blood was collected and processed as described above. Levels of plasma Aβ42 were determined at 6 hours post injection using an Aβ42-specific ELISA kit (Life Technologies) according to the manufacturer's instructions.

Transmission Electron Microscopy (TEM). Samples were diluted to 0.1 mg/ml, applied to glow discharged CF200-Cu grids (Electron Microscopy Sciences), washed three times with ultrapure water, and negatively stained with 2% uranyl acetate. Images were acquired using a JEOL JEM 100CX Transmission Microscope at The Rockefeller University Electron Microscopy Resource Center.

Statistical Analysis. Comparisons between groups were performed using the two-tailed Mann-Whitney test for non-parametric data. Comparisons between multiple groups were performed using Kruskal-Wallis test followed by Dunn's Multiple Comparison Test. Comparisons of kallikrein-like activity between groups were performed using the one-tailed Mann-Whitney test. For intravenous injection experiments, comparisons between groups were performed using ANOVA followed by Dunnett's Multiple Comparison Test for multiple groups with a single control. Data are presented as vertical scatter plots with medians and reported as medians or means±standard deviation in the text. Correlations between CSF biomarker measures, kallikrein-like activity, and Western blot results were examined using Pearson's correlation coefficient (r). P values≤0.05 were considered significant (*), with values≤0.01 designated (), values≤0.001 designated (*), and values≤0.0001 designated (****) in the figures. Analyses were performed using Graph-Pad Prism 5 software.

Example 7

Examples 7-12 demonstrate, among other features, that AP oligomers promote coagulation by inducing FXII-mediated thrombin generation through the intrinsic coagulation pathway. We demonstrate the relevance of these findings to AD by showing decreased plasma levels of FXI and its inhibitor C1 esterase inhibitor (C1inh) as well as increased levels of fibrin in AD patient plasma, suggesting activation of FXI and the intrinsic coagulation pathway.

Figure 12:
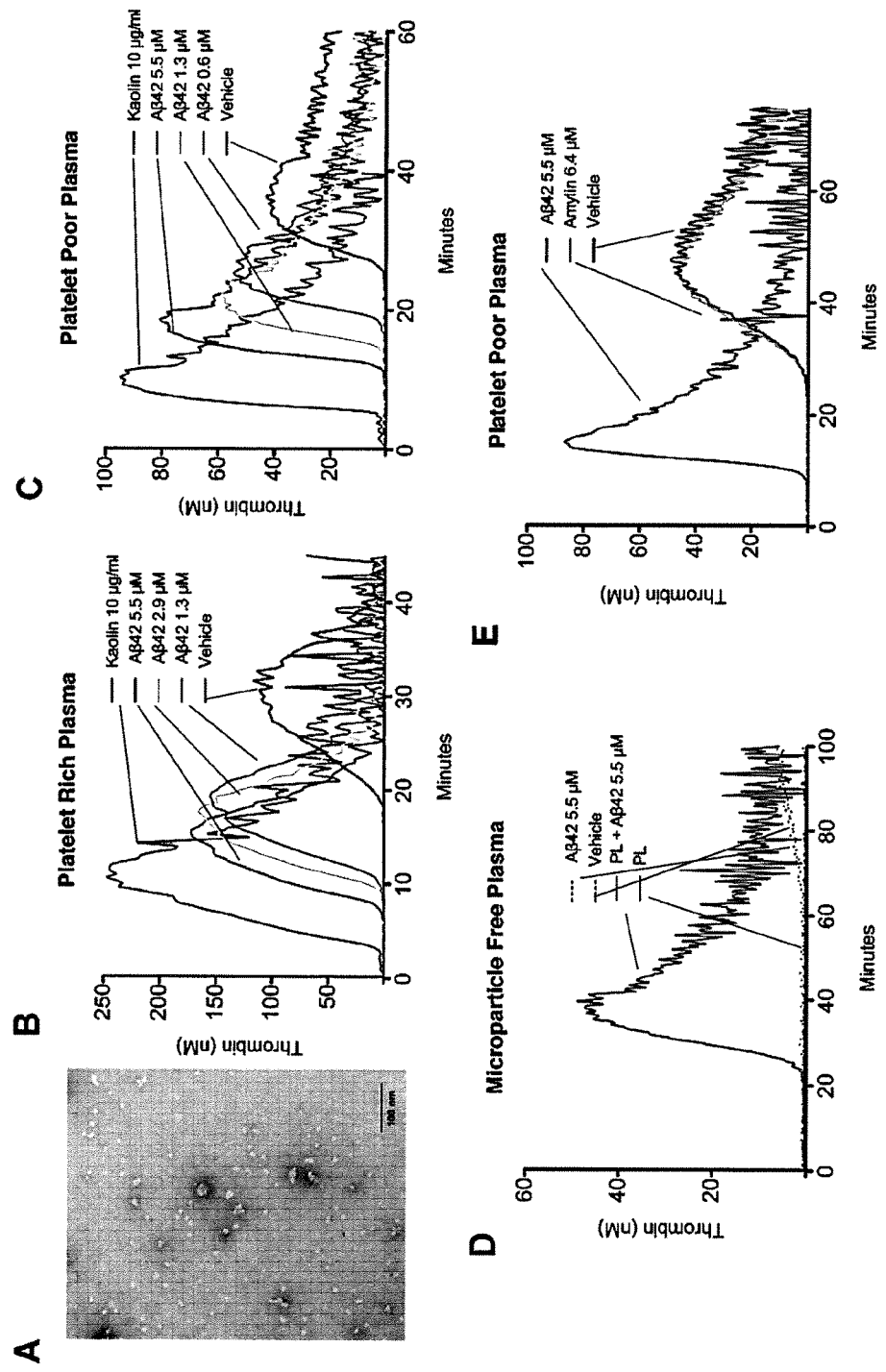
FIG. 12. Aβ42 triggers thrombin generation in human plasma. (A) Representative TEM image of Aβ42 oligomers used. (B-E) Real-time thrombin generation was measured by CAT. (B) Platelet rich plasma (PRP) was incubated with Aβ42 at concentrations indicated or kaolin (a known activator of thrombin generation). Lag time to thrombin generation was decreased and thrombin peak was increased in the presence of Aβ42 in a dose-dependent manner. (C) As in (B), except platelet poor plasma (PPP) was used. (D) Aβ42 had no effect in platelet- and microparticle-free plasma. Addition of phospholipids (PL; 4 μM) restored Aβ42's ability to trigger thrombin generation. (E) Lag time to thrombin generation was decreased and maximum peak height was increased in PPP with Aβ42 but not amylin. All experiments were performed in duplicate, and averaged curves are presented.

Aβ42 promotes thrombin generation in plasma. To determine if Aβ42 is prothrombotic, we quantified thrombin generation in human plasma using the Calibrated Automated Thrombogram (CAT) in the presence of oligomeric Aβ42, a toxic assembly that correlates with disease severity. The oligomeric composition of Aβ42, which is stable for 24 hrs at RT and 37° C. (FIG. 17), was confirmed by electron microscopy (FIG. 12A). In the absence of exogenous activators, a small thrombin burst is detectable after a long lag period (Vehicle, FIG. 12B). Addition of Aβ42 to PRP promoted thrombin generation in a dose-dependent manner, as indicated by a shortening of the lag time to thrombin burst and an increase in peak height (maximum thrombin formed) (FIG. 12B). A similar prothrombotic effect was observed in PPP (FIG. 12C), indicating that platelets are not required for the effect. However, Aβ42 had no effect in microparticle-free plasma (FIG. 12D). Supplementing microparticle-free plasma with phospholipids restored Aβ42's ability to trigger thrombin generation (FIG. 12D), indicating that the presence of phospholipid surfaces (found on platelets and microparticles) is required for Aβ42-mediated thrombin generation. The prothrombotic effect is specific to Aβ42, since amylin, another amyloid-forming peptide, failed to induce thrombin generation (FIG. 12E).

Example 8

This Example demonstrates that Aβ42-mediated thrombin generation is FXII-dependent. Thrombin is generated through the activation of the intrinsic (FXII-driven) or extrinsic (tissue factor; TF-driven) coagulation pathways. To determine which pathway is activated by Aβ42, CAT experiments were performed in the presence of a FXIIa function blocking antibody (to block the intrinsic pathway), or with active site-inhibited factor VII (ASIS; to block the extrinsic pathway). The FXIIa antibody abolished Aβ42-induced thrombin generation (FIG. 13A), whereas ASIS had no inhibitory effect (FIG. 13B), indicating that Aβ42 is prothrombotic via the FXIIa-driven intrinsic coagulation pathway. The FXIIa antibody specifically blocks FXIIa-mediated thrombin generation, since it abolished thrombin generation initiated by kaolin (a FXII activator) but did not interfere with TF-initiated thrombin generation. As expected, ASIS inhibited TF-initiated thrombin generation (FIG. 18).

Figure 13:
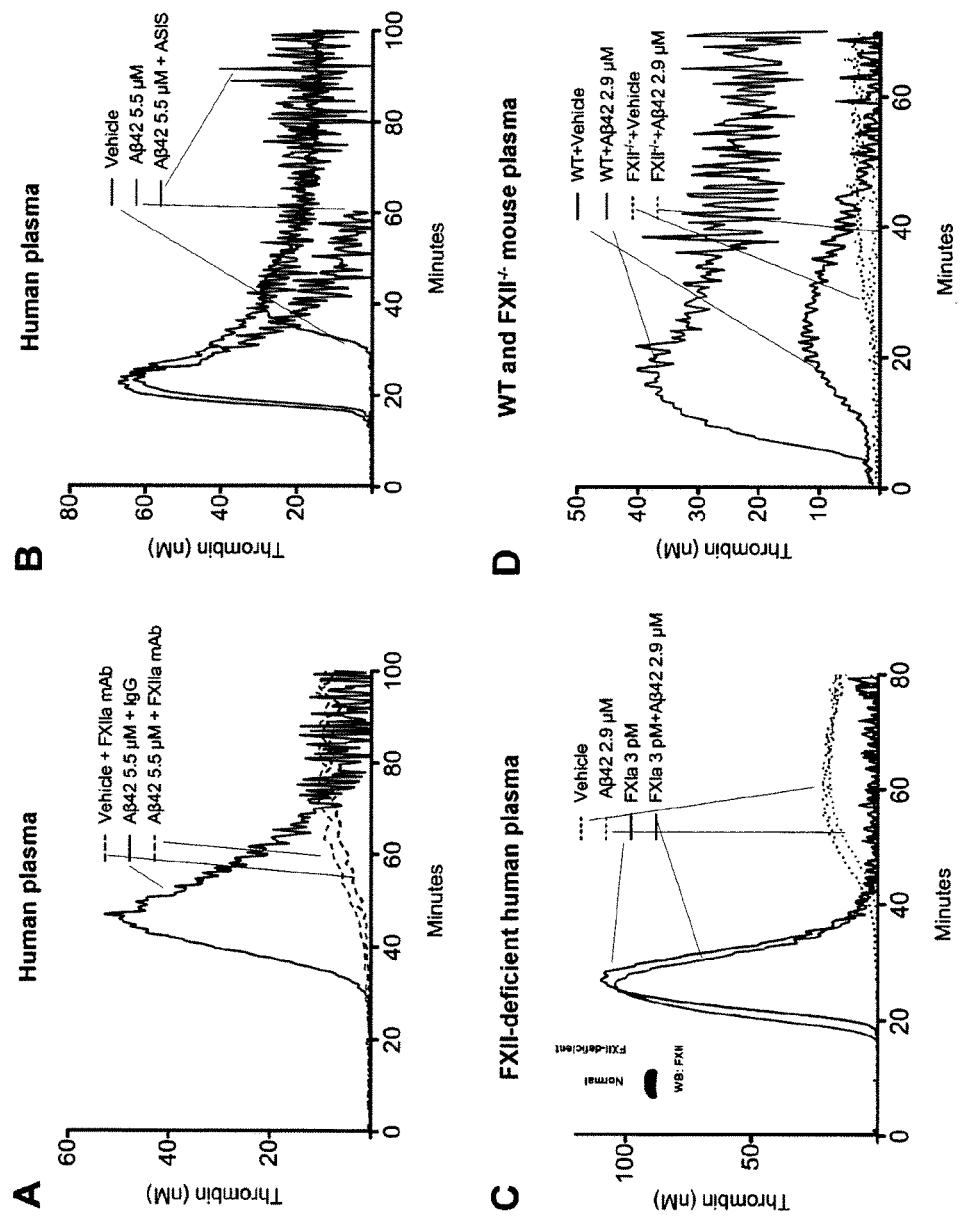
FIG. 13. Aβ42 promotes thrombin generation in a FXII-dependent manner. Thrombin generation was measured by CAT. (A) Aβ42-induced thrombin generation was blocked by a monoclonal antibody against FXIIa (4 μM), but not by IgG. (B) Aβ42's enhancement of thrombin generation was not inhibited by the extrinsic coagulation pathway inhibitor ASIS (60 nM). (C) Thrombin generation was not enhanced in human plasma from a FXII-deficient individual in the presence of Aβ42. Deficiency of FXII in this plasma was confirmed by Western blot (WB; inset). Aβ42 had no effect when thrombin generation was triggered by 3 pM FXIa. (D) Thrombin generation was enhanced in WT mouse plasma but not FXII−/− mouse plasma in the presence of Aβ42. Mouse plasma contained 240 nM ASIS to block TF-mediated thrombin generation stemming from TF contamination during blood draw. ASIS does not affect Aβ42-mediated enhancement of thrombin generation (FIG. 12B). All experiments were performed in duplicate, and averaged curves are presented.
Figure 14:
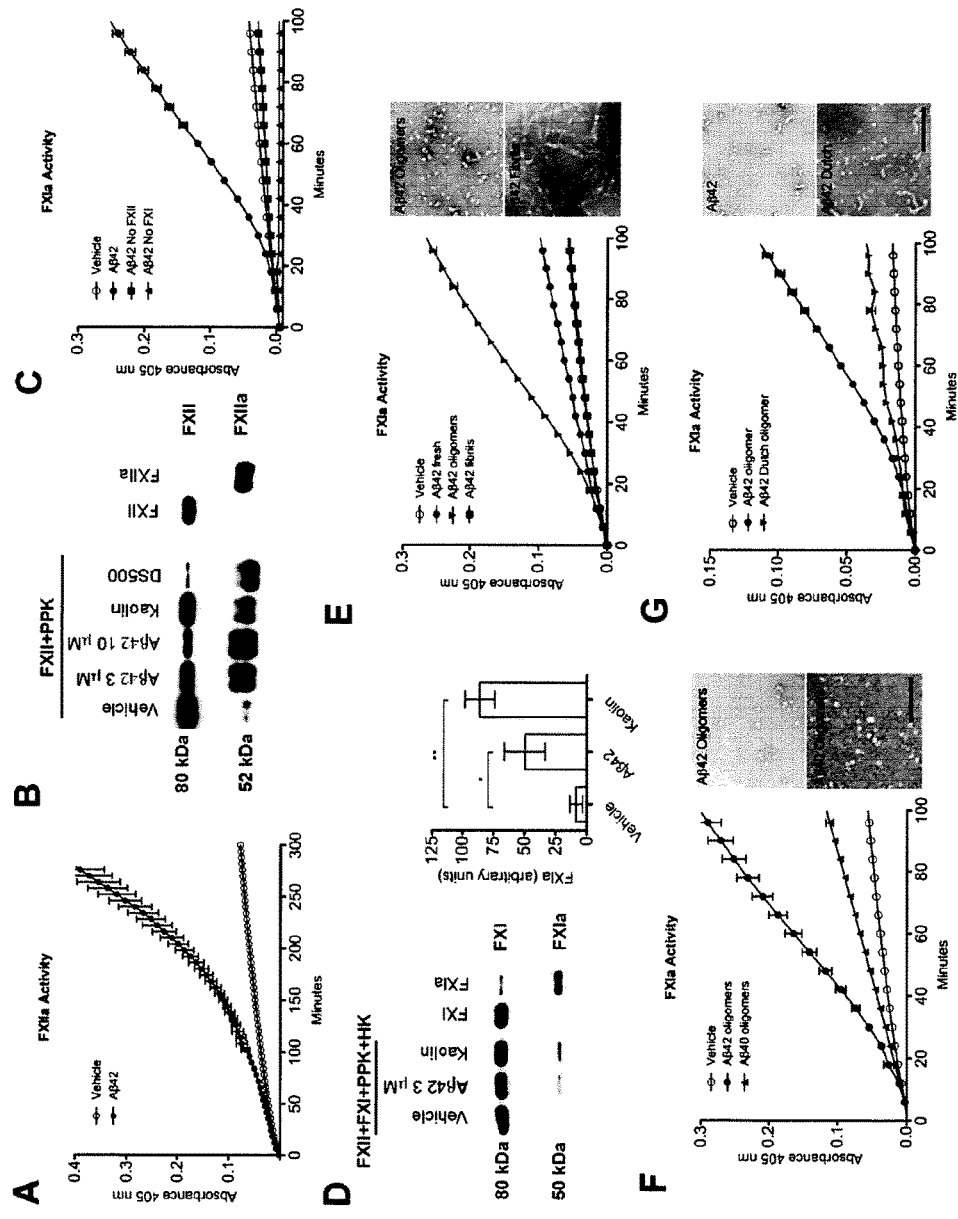
FIG. 14. Aβ promotes FXII-dependent FXI activation in vitro. (A) Aβ42 (3 μM) triggered autoactivation of FXII as determined by chromogenic substrate assay. (B) In the presence of both FXII and prekallikrein (PPK), Aβ42 dose-dependently promoted activation of FXII as seen through the reduction of FXII zymogen levels at 80 kDa and the appearance of the FXIIa heavy chain at 52 kDa. Dextran sulfate 500 kDa (DS500) and kaolin were used as positive controls. (C) Aβ42 (3 μM) triggered FXII-dependent FXIa generation by chromogenic substrate assay. The signal was not due to non-specific cleavage of chromogenic substrate by FXIIa, or by autoactivation of FXI, as seen in controls where FXII or FXI were omitted. (D) FXI activation can be seen through the appearance of the 50 kDa FXIa heavy chain band following incubation of FXII, FXI, PPK, and HK with Aβ42 or kaolin. Levels of FXIa heavy chain were increased in Aβ42-(p<0.05) and kaolin-(p<0.01) treated samples compared to vehicle. All lanes presented are from the same blot. (E) Aβ42 oligomers were more potent in promoting FXII-dependent FXI activation than freshly dissolved Aβ42. Aβ42 fibrils had no effect. All Aβ42 preparations were 3 μM. (F) Aβ42 oligomers were more potent than A340 oligomers in promoting FXII-dependent FXI activation. (G) Aβ42 oligomers (TEM image, top inset) promoted FXII-dependent FXI activation much more strongly than Aβ42 Dutch oligomers (TEM image, bottom inset). Chromogenic substrate assays were performed multiple times with representative results shown. Representative immunoblots are from 3 experiments.

To further examine the role of FXII in Aβ42-mediated thrombin generation, we analyzed the effect of Aβ42 in FXII-deficient human plasma (with no detectable plasma FXII antigen; FIG. 13C inset). Aβ42 failed to trigger thrombin generation in FXII-deficient plasma (FIG. 13C, dashed curves). To examine the role of Aβ42 in a system where FXII is completely absent, we tested plasma from mice that do not express any FXII (FXII−/−). While Aβ42 promoted thrombin generation in WT mouse plasma, no effect was seen in FXII−/− mouse plasma (FIG. 13D).

Since FXII-deficient or -neutralized plasmas have normal levels of downstream coagulation factors, the results also indicate that thrombin generation is not driven through direct activation of these factors by Aβ42. However, Aβ42 may potentiate downstream factors when they are in the activated state, which may be produced by low-level, well surface-mediated FXII activation (e.g. the background thrombin signal in FIG. 11A). To address this possibility, thrombin generation in FXII-deficient human plasma was measured following activation with FXIa, which activates downstream members of the coagulation cascade. Aβ42 had no effect on thrombin generation in plasma activated with low levels of FXIa (FIG. 13C, solid curves), indicating that it does not enhance the activity of FXIa or any downstream factors. Furthermore, Aβ42 had no effect on thrombin generation in plasma from mice that have normal levels of FXII but do not express FXI (FIG. 19), confirming that the pathway enhanced by Aβ42 involves FXIIa-mediated activation of FXI and not FXIIa-mediated activation of another substrate.

Example 9

Figure 15:
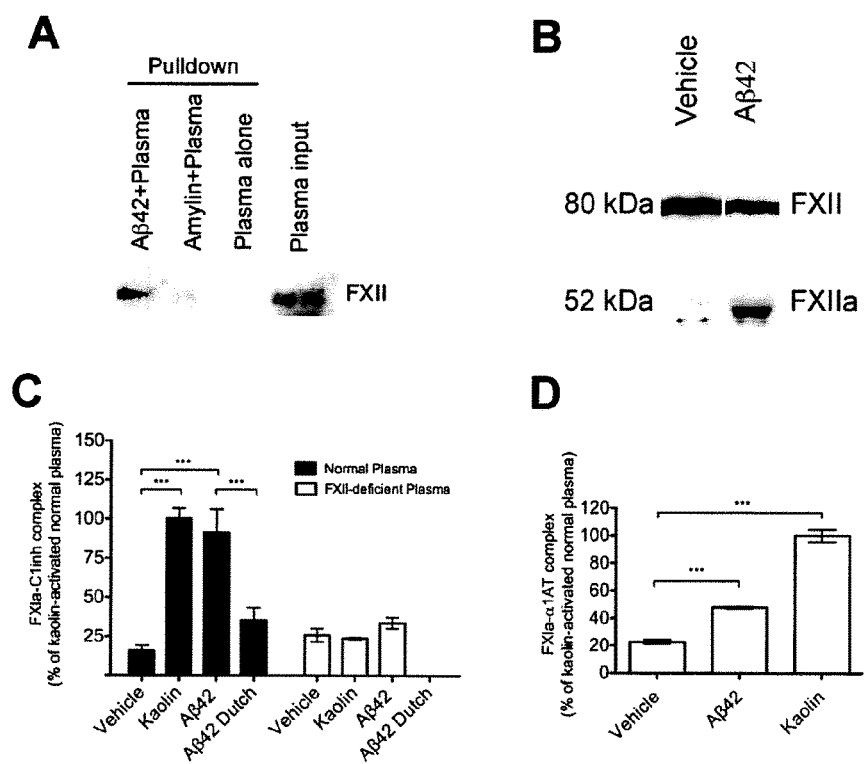
FIG. 15. Aβ42 promotes FXII-dependent FXI activation in plasma. (A) Western blot demonstrating that biotinylated Aβ42 oligomers pull down FXII from human plasma. (B) Incubation of Aβ42 oligomers with human plasma leads to FXII cleavage. (C) ELISA measuring FXIa-CIinh complex formation in normal and FXII-deficient human plasma. Oligomers of Aβ42 but not Aβ42 Dutch promoted the formation FXIa-CIinh (p<0.001; Aβ42 vs. vehicle). (D) ELISA measuring FXIa-α1AT complex formation in normal human plasma. Aβ42 oligomers promoted increased FXIa-α1AT complex formation (p<0.0001; Aβ42 vs. vehicle). Results are expressed as % of kaolin-activated normal plasma and presented as mean±SD of experiments performed in triplicate.

This Example demonstrates that AP triggers FXII-dependent FXI activation in vitro. FXII undergoes autoactivation on negatively charged surfaces. Since autoactivation of FXII has only been shown with fibrillar Aβ40 and in the presence of ZnC12 [Shibayama et al., 1999, Clin Immunol, 89-99], we first determined that Aβ42 oligomers can directly induce FXII autoactivation (FIG. 15A). Physiologically, contact system activation takes place in the presence of prekallikrein, which is activated by FXIIa to kallikrein, which in turn activates additional FXII, amplifying the reaction. Aβ42 dose-dependently promoted FXII activation in the presence of prekallikrein (FIG. 15B), as seen through the reduction of FXII zymogen levels (80 kDa) and the appearance of the FXIIa heavy chain (52 kDa).

Aβ42 led to FXIIa-dependent FXIa generation in the absence (FIG. 15C) and presence (FIG. 15D) of prekallikrein, indicating that FXII activated by Aβ42 is capable of cleaving its substrate FXI. Previously, FXIIa-dependent FXI activation and procoagulant effects were not detected in the presence of Aβ [Maas et al., 2008; J Clin Invest, 3208-18]. The main difference between our experiments is that the previous study used "amorphous aggregates" of Aβ42 with the Dutch mutation (E22Q) instead of the wild-type oligomeric Aβ42 used here. This discrepancy prompted us to analyze the ability of Aβ42 in different states of aggregation as well as other Aβ variants to trigger FXII-dependent FXI activation. We found that Aβ42 oligomers had a much greater ability to trigger FXII-dependent FXI activation than freshly dissolved Aβ42 (FIG. 15E) or Aβ40 oligomers (FIG. 15F), while Aβ42 fibrils produced no FXI activity at all (FIG. 15E). Furthermore, even the most active (oligomeric) form of Aβ42 Dutch was substantially less potent than oligomeric Aβ42 in stimulating FXII-dependent FXI activation (FIG. 15G), indicating that the discrepancy between our results is due to the use of Aβ42 Dutch and the different state of Aβ aggregation in the previous study.

Example 10

This Example demonstrates that Aβ42 oligomers trigger FXII-dependent FXI activation in plasma. We next examined FXII-mediated FXI activation by Aβ42 in human plasma. Biotinylated Aβ42 (TEM of oligomeric preparation in FIG. 20), but not biotinylated amylin, was able to bind FXII in plasma as shown by pulldown assay (FIG. 15A), demonstrating that the Aβ42-FXII interaction is specific and occurs in the presence of plasma proteins. This interaction leads to FXII activation, since plasma incubated with Aβ42 had decreased FXII zymogen and increased FXIIa heavy chain compared to incubation with vehicle (FIG. 15B). Activation of FXI in plasma can be sensitively measured by quantifying FXIa-inhibitor complex levels, since FXIa generated in plasma is rapidly bound by inhibitors [48]. Incubation of plasma with Aβ42 but not Aβ42 Dutch oligomers resulted in increased levels FXIa-C1 inhibitor (C1inh) complex (FIG. 15C; p<0.001). The activation of FXI by Aβ42 was FXII-dependent, since Aβ42 did not promote FXIa-C1inh complex formation in FXII-deficient plasma. The levels of FXIa in complex with al antitrypsin (α1AT), another FXIa inhibitor, were also increased in plasma following activation with Aβ42 (FIG. 15D; p<0.0001).

Example 11

Figure 16:
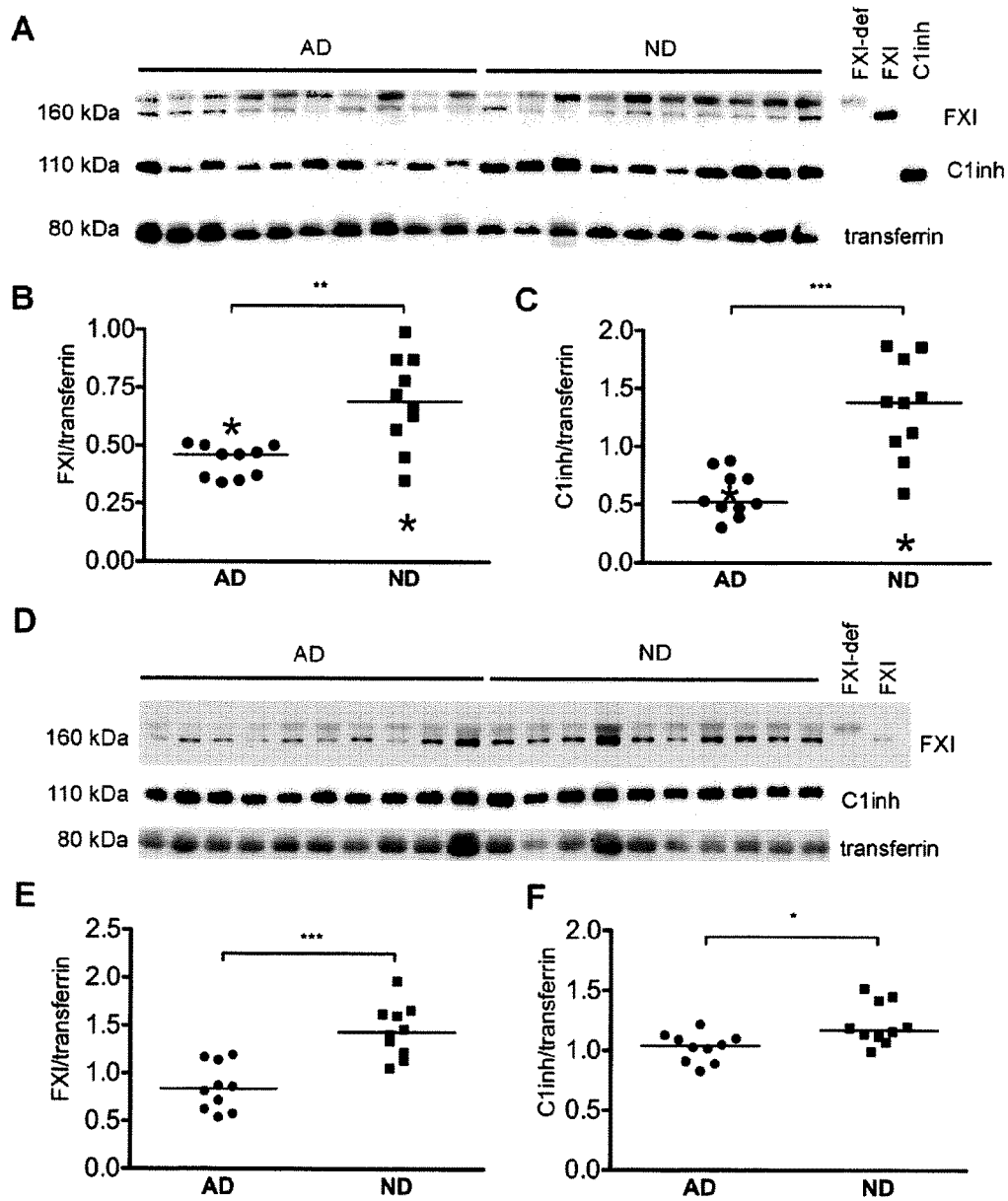
FIG. 16. AD patient plasma has lower levels of FXI and Clinh and increased levels of fibrin. (A) Non-reducing Western blot analysis of FXI, Clinh, and transferrin loading control in plasma of 10 AD patients and 10 ND controls from Group 1. Lanes loaded with FXI purified protein (FXI)
Figure 16:
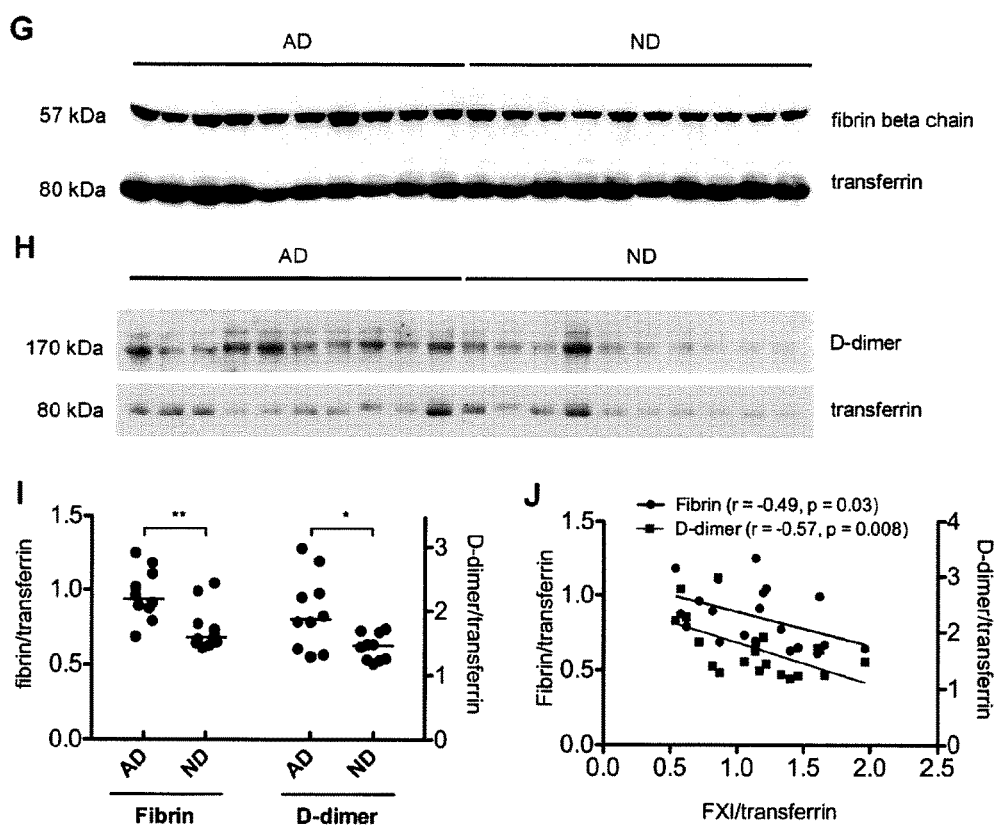

This Example demonstrates that levels of FXI zymogen and C1inh are decreased and levels of fibrin are increased in AD patient plasma. We next investigated whether the FXII-driven intrinsic coagulation pathway is activated in AD patient plasma. Two sets of AD patient and non-demented control (ND) plasmas were obtained from two plasma banks. Group 1 consisted of 10 AD and 10 ND samples matched with respect to age, gender, and ApoE genotype (Table 4), and Group 2 consisted of 10 AD and 10 ND samples matched with respect to age (Table 5). Plasma was analyzed by Western blot, with results normalized to transferrin loading control, levels of which are unchanged in AD patients [Squitti et al., 2010, 231595]. Increased activation of FXI in plasma can be detected as decreased plasma FXI zymogen levels, often observed in disease states accompanied by FXI activation, with decreased plasma FXI zymogen levels possibly reflecting continuous consumption of FXI due to its activation and clearance. AD plasma had decreased levels of FXI zymogen compared to ND plasma in both Group 1 (0.46 [0.36-0.50] vs. 0.69 [0.54-0.87], p=0.008; FIG. 16A,B) and Group 2 (0.84 [0.61-1.15] vs. 1.43 [1.20-1.96], p=0.0003; FIG. 16D,E).

If AD plasma FXI levels are decreased due to its activation and clearance, levels of its main inhibitor C1inh [48] would also be expected to decrease. Indeed, C1inh levels were decreased in AD vs. ND plasma in both Group 1 (0.52 [0.45-0.75] vs. 1.39 [1.01-1.79], p=0.0008; FIG. 16A,C) and Group 2 (1.04 [0.91-1.11] vs. 1.18 [1.11-1.43], p=0.012; FIG. 16D,F), suggesting its consumption. Decreased levels of FXI and C1inh in AD vs. ND control plasma were accompanied by increased levels of FXIIa (FXIIa levels were derived from results presented in in Examples 1-6 and are designated by asterisks in FIG. 16B,C). This relationship suggests that depletion of FXI and C1inh in AD patient plasma is due to FXII activation.

Activation of the intrinsic pathway of coagulation would be expected to result in increased thrombin generation and fibrin formation. Indeed, AD patients from Group 2 had elevated plasma fibrin (0.94 [0.85-1.13] vs. 0.68 [0.64-0.83], p=0.009); and D-dimer (1.88 [1.39-2.41] vs. 1.46 [1.24-1.68], p=0.018) levels compared to controls (FIG. 16G-I). Levels of fibrin and D-dimer were inversely correlated with FXI levels (r=−0.46, p=0.04 for fibrin; r=−0.57, p=0.008 for D-dimer, FIG. 16J), suggesting that activation and subsequent clearance of FXI results in thrombin generation and fibrin formation. In Group 1, there was a non-significant trend toward increased fibrin levels in AD plasma (not shown), which could be due to differences in blood draw and anticoagulation methods between the groups (see Methods). Another possible explanation is the more advanced disease stage of patients in Group 1 compared to Group 2 as determined by Clinical Dementia Rating score measuring cognitive function, where 0=no dementia and 3=severe dementia [Morris, 1993] (2.0±1.1 for Group 1 vs. 1.0±0.6 for Group 2, p=0.028; Tables 4 and 5). Since Group 1 patients are likely to have been exposed to FXI activation for longer due to more advanced disease, the fibrin formed may have been progressively deposited, thereby depleting soluble fibrin from plasma.

TABLE 4

Characteristics of AD and ND cases from Group 1 of this Example

| | Group (n) | |
|---|---|---|
| | AD (10) | ND (10) |
| Mean age at blood draw (years; SD) | 80.0 (9.0) | 81.7 (6.1) |
| Gender (% Male) | 50 | 60 |
| ApoE genotype 3/3 (%) | 100 | 100 |
| Mean CDR score at blood draw (score; SD) | 2.0 (1.1) | 0.1 (0.2) |
| CERAD (%) | | |
| None | 0 | 100 |
| B | 30 | 0 |
| C | 70 | 0 |
| Braak stage (%) | | |
| 0-2 | 0 | 100 |
| 3-4 | 10 | 0 |
| 5-6 | 90 | 0 |

TABLE 5

Characteristics of AD and ND cases from Group 2 of this Example

| | Group (n) | |
|---|---|---|
| | AD (10) | ND (10) |
| Mean age at blood draw (years; SD) | 73.6 (5.8) | 70.5 (3.9) |
| Gender (% Male) | 30 | 50 |
| Mean CDR score at blood draw (score; SD) | 1.0 (0.6) | 0.0 (0.0) |

Our results identify Aβ as a prothrombotic factor that can trigger thrombin generation via FXII-dependent activation of FXI. Aβ42-mediated, FXII-dependent FXI activation was previously not found (Maas C, et al., J Clin Invest. 2008; 118: 3208-18), likely because amorphous aggregates of Aβ42 with the Dutch mutation (E22Q) were used. While that study found no FXI activation with Aβ42 Dutch amorphous aggregates, our results with Aβ42 Dutch oligomers showed low levels of FXII-dependent FXI activation, highlighting the importance of the assembly state of Aβ42 Dutch in FXI activation. We also showed that wild-type oligomeric Aβ42 was a more potent FXI activator than monomeric and fibrillar preparations, further supporting the importance of AP aggregation state. Finally, wild-type Aβ42 oligomers were much more potent in FXI activation than Aβ42 Dutch oligomers, possibly due to differences in peptide charge (−2.7 for Aβ42 vs. −1.7 for Aβ42 Dutch at pH 7). More negative charge and/or the presence of glutamic acid at position 22 of Aβ42 therefore appears crucial for its activation of FXII and FXI, and it is possible that this region is more optimally exposed in oligomers. In AD and pre-AD states, circulating Aβ may induce chronic, low-level FXII-dependent FXI activation. This is supported by increased FXIIa levels (FIG. 1A,B) and decreased levels of FXI zymogen and its inhibitor C1inh in AD patient plasma (FIG. 16), which could reflect the clearance of the FXIa-C1inh complex following FXII-dependent FXI activation. Chronic FXI activation could mediate the production of low "idling" levels of thrombin, which may contribute to the chronic formation of fibrin, supported by increased fibrin monomer and D-dimer levels in the plasma of AD patients from Group 2.

Example 12

This Example is a description of the materials and methods used to produce the data described herein.

Aβ preparation. Aβ42, Aβ40, and Aβ42 E22Q Dutch (Anaspec) monomers and oligomers were prepared as in [Stine W B, et al. Methods Mol Biol. 2011; 670: 13-32]. For fibrils, Aβ42 was dissolved in 60 μl 1% NH4OH, adjusted to 200 Mm with 50 Mm Tris Ph 7.4, 150 Mm NaCl and incubated at 37° C., shaking, for 7 days. Aβ preparations were confirmed by transmission electron microscopy (TEM) at Rockefeller University's Electron Microscopy Resource Center.

Blood collection and plasma preparation. Experiments with human plasma were approved by Rockefeller's Institutional Review Board. Blood was drawn from healthy volunteers giving informed, written consent using 21 gauge 0.75 inch butterfly needles (BD) with a multi-adapter for S-Monovette (Sarstedt) into S-Monovette tubes containing 1/10 volume 0.106 Mm trisodium citrate solution at Rockefeller University Hospital and Karolinska Institute Hospital. To obtain platelet rich plasma (PRP), blood was centrifuged at 130×g for 10 min, and the top ½ of the PRP removed. To obtain platelet poor plasma (PPP), blood was centrifuged twice at 2000×g for 10 min. PPP was frozen immediately at −80° C. Microparticle-free plasma was prepared by ultracentrifugation at 100,000×g for 30 min at 4° C.

Mouse lines. Animal care and experimental procedures complied with the principles of laboratory and animal care established by the National Society for Medical Research and were approved by the Stockholms Norra Djurförsöksetiska Nämnd. FXII−/− and FXI−/− mice backcrossed to C57BL/6 mice for >10 generations and age-matched C57BL/6 control mice (Charles River) were used. Blood was collected using repel-gel (Sigma) coated glass capillary tubes into citrated Eppendorf tubes. PPP was prepared by centrifugation at 1500×g for 15 min.

Thrombin generation in plasma. Thrombin generation in normal or FXII-deficient human plasma (George King Biomedical) was measured by Calibrated Automated Thrombogram (CAT) using known techniques. In some cases, plasma was pre-incubated for 30 min with a FXIIa antibody [42] or active-site inhibited factor VII (ASIS; Novo Nordisk). Some reactions also contained FXIa (Haematologic Technologies; 3 Pm) or phospholipids (Thrombinoscope BV; 4 Mm). Thrombin generation in FXII-/-, FXI-/-, and C57BL/6 mouse plasma was measured as described above with known modifications.

Aβ42-FXII binding. Human plasma diluted 1:5 in PBS containing 0.01% NP-40 and protease inhibitor cocktail (Roche) was incubated with 500 Nm biotinylated Aβ42 or amylin (Anaspec) for 2 hrs at RT followed by pulldown with streptavidin Dynabeads M-280 (Life Technologies), then analysis by Western blot using monoclonal antibody against FXII (Haematologic Technologies).

FXII and FXI activation in vitro and in plasma. Chromogenic substrate: For FXII activation, 0.8 Mm Pefachrome FXIIa (Centerchem), was added to 100 Nm FXII (Haematologic Technologies) and 3 μM Aβ or vehicle. For FXII-dependent FXI activation, 0.8 Mm Pefachrome FXIa (Centerchem) was added to 5 Nm FXII, 15 Nm FXI (Haematologic Technologies), and 3 μM Aβ or vehicle. Activity was monitored at 405 nm using a Molecular Devices Spectramax Plus 384 reader at 37° C. in 96-well polystyrene plates (Fisher Scientific) pre-coated with 1% Polyethylene glycol 20,000 in 20 Mm HEPES containing 140 Mm NaC1 (HEPES-buffered saline; HBS).

Western blot: For FXII activation, FXII (200 Nm) and prekallikrein (150 Nm) were incubated with Aβ42 (3 μM), dextran sulfate 500 kDa (DS500; Sigma; 10 μg/ml), or vehicle for 30 min at 37° C. For FXI activation, FXII (200 Nm), prekallikrein (150 Nm), HK (Molecular Innovations; 300 Nm), and FXI (150 Nm) were incubated with Aβ (3 μM), kaolin (Fisher; 100 μg/ml), or vehicle for 30 min at 37° C. Plasma from healthy volunteers was diluted 1:10 in HBS and incubated with Aβ42 (20 Mm) for 1 hour at 37° C. Reactions were stopped by adding reducing sample buffer and heating for 5 min at 85° C. Blots were probed with antibodies against FXII and FXI (Hematologic Technologies; HTI). FXI activation was quantified using densitometric analysis.

ELISA measuring FXIa-inhibitor complex formation: Normal or FXII-deficient human plasma was diluted 1:10 in HBS and incubated with Aβ42, Aβ42 Dutch (20 μM), kaolin (10 μg/m1), or vehicle at 37° C. for 1 hr. Reactions were transferred to a plate pre-coated with a FXI monoclonal antibody (3 μg/ml; HTI) and blocked with PBS containing 2% milk (blocking buffer) for 1 hr. Following 1 hr incubation, wells were washed 3×5 min with PBS containing 0.05% Tween-20. A polyclonal C1 inhibitor (3 μg/ml; Cedarlane) or alpha-1-antitrypsin (3 μg/ml; Thermo Scientific) antibody in blocking buffer was applied for 1 hr. After washing, an HRP-conjugated anti-goat antibody (Jackson; 1:2000) in blocking buffer was applied for 1 hr. The ELISA was developed with TMB peroxidase substrate (Thermo Scientific).

FXI, C1 esterase inhibitor, and fibrin levels in human plasma. Plasma from AD patients and non-demented (ND) controls was obtained from the University of Kentucky Sanders-Brown Center on Aging (Group 1) and Washington University Knight Alzheimer's Disease Research Center (Group 2). Group 1 AD cases were defined by clinical diagnosis of AD as well as postmortem Consortium to Establish a Registry for Alzheimer's Disease (CERAD) neuritic plaque score [Mirra et al] of B or C, corresponding to probable or definite AD, respectively. ND cases had CERAD score 0 and no clinical diagnosis of AD (Table 4). Group 2 AD cases had a Clinical Dementia Rating score (CDR; measuring cognitive function) [Morris, 1993] of ≥0.5 and CSF Aβ42 levels<500 pg/ml, and ND cases had a CDR score of 0 and CSF Aβ42 levels >500 pg/ml (Table 5). For Group 1, blood was drawn into heparinized plastic Vacutainer tubes. For Group 2, blood was drawn using EDTA-coated syringes into polypropylene tubes containing a final concentration of 5 Mm EDTA.

Equal amounts of total protein from each sample (as determined by BCA) were analyzed by Western blot with antibodies against FXI (HTI), C1 esterase inhibitor (Proteintech), fibrin beta chain (59D8), D-dimer (AbD Serotec) and transferrin (Abcam). Purified FXI, C1 esterase inhibitor (Athens Research and Technology), and FXI-deficient plasma (George King Biomedical) served as controls.

Statistical Analysis. Data are presented as vertical scatter plots with medians and reported as medians with $25^{th}$ and $75^{th}$ percentile ranges (median [$25^{th}$-$75^{th}$ percentile range]), or presented as bar graphs (mean±SD). Comparisons between groups were performed using the unpaired, two-tailed Mann-Whitney test or one-way ANOVA followed by Tukey's Multiple Comparison Test. Correlation was analyzed using Spearman's correlation Coefficient®. P values≤0.05 were considered significant (*), with values≤0.01 designated (), and values≤0.001 designated (*). Statistical analyses were performed using GraphPad Prism 5.

Example 13

This Example provides a description of making and using antibodies in diagnostic methods, and for use in kits of this disclosure. It particularly provides a description of hybridomas, immunogens, and methods of using antibodies produced by the hybridomas in immunological detection assays for HK and HKc for diagnosing, or aiding in the diagnosis of, AD.

Antibodies. The disclosure includes antibodies produced by the hybridoma referred to as "3E8." For convenience the monoclonal antibodies produced by this hybridoma are referred to by the same term. As described further below, 3E8 detects both HK and HKc, and thus in one non-limiting embodiment can be used as a capture antibody in, for example, an ELISA assay. To obtain 3E8, the peptide corresponding to residues 563-581 of human high molecular weight kininogen (IQSDDDWIPDIQIDPNGLSC—SEQ ID NO:6), with the terminal cysteine added for coupling) was synthesized at the Rockefeller University Proteomics Resource Center. The peptide was then conjugated to keyhole limpet hemocyanin (KLH) and injected into 4 Armenian hamsters at the Rockefeller University Tri-Institutional Monoclonal Antibody Resource Center. Hamsters received 3 boost immunizations. B cells from hamster spleens were isolated and fused with immortalized myeloma cells. Hybridomas were screened to identify those producing antibodies that recognize HK and HKc equally well in solution. Hybridomas were cloned and the antibody was purified. Thus, the 3E8 mAb binds with specificity to a peptide consisting of the sequence of SEQ ID NO:6. As described here and elsewhere in this disclosure, 3E8 binds both HK and HKc.

The disclosure also includes 2B7, which binds with specificity to HK only, and therefore does not bind with specificity to HKc. As such, in certain non-limiting implementations of the present disclosure, it is suitable for use as, for example, a detection antibody in an ELISA assay. To obtain 2B7, purified full length human HK and cleaved HK were used to immunize hamsters. Hybridomas were screened to identify those producing antibodies that recognize HK but not HKc in solution. Thus, the present disclosure includes mAb 3E8 that binds with specificity to HK, but does not bind with specificity to HKc. Further, the disclosure comprises hybridomas and mAbs produced by them which are termed 6A6-B, 12E5-A, and 15D9. Each of these bind with specificity to both HK and HKc. Thus, they are suitable for using, for example, as detection antibodies for total HK measurements, and for detection of HKc following clearance of samples with, for example, 2B7. To obtain 6A6-B, 12E5-A, and 15D9, purified full length human HK and cleaved HK were used to immunize hamsters and produce hybidomas. Hybridomas were screened to identify those producing antibodies that recognize HK and HKc equally well in solution. The disclosure thus includes the following mAbs: 3E8, which detects both HK and HKc and is therefore suitable for use as a capture antibody, among other uses; 2B7, which detects HK but not HKc, and is therefore suitable for use as a detection antibody, among other uses, and 6A6-B, 12E5-A, 15D9, each of which detect both HK and HKc, and thus are suitable for use as detection antibodies for total HK measurements, and for detection of HKc following clearance of samples with, for example, 2B7.

We demonstrate the utility of mAbs of this disclosure using 3E8 as a representative capture antibody and 2B7 as a representative detecting antibody, as follows.

ELISA design: The ELISA for detection of intact HK in human plasma will consist of a capture antibody that binds both HK and HKc, a plasma sample containing an unknown mixture of HK and HKc, and a labeled detection antibody that only detects HK. The ELISA will determine the amount of HK in the sample based on a standard curve using purified HK. The ELISA may or may not be combined with another ELISA determining the total amount of HK (HK+HKc) in the plasma sample, from which the amount of intact HK can be subtracted to determine HKc levels. A schematic providing a non-limiting representation of an embodiment of the disclosure is presented in FIG. 21.

ELISA capture antibody: Hybridoma media containing potential capture antibodies were tested for their ability to bind HK and HKc in solution. Antibodies from the conditioned media were immobilized on Protein G plates, and the antibodies were exposed to HK, HKc, or buffer. A commercially available HRP-conjugated detection antibody was then used to quantify the amount of HK or HKc captured. We selected the cell line 3E8 for capture antibody production based on its strong ability to bind both HK and HKc (FIG. 22).

ELISA detection antibody: Purified capture antibody 3E8 was immobilized on a 96-well ELISA plate (at 100 ng/well in 0.1 M Sodium Bicarbonate buffer pH 9.6 at 4° C. overnight). Wells were washed 3× with PBS+0.1% Tween-20 (PBS-T) and blocked with 100 µl PBS+0.1% Tween-20+ 1% BSA+0.02% NaN3 (blocking buffer) for 1 hour at room temperature. Following 3× wash with PBS-T, known amounts of HK or HKc (Molecular Innovations; 0-120 pM) were applied for 1 hour at room temperature. Following 3× wash with PBS-T, 50 µl biotinylated detection antibody 2B7 was added at 0.05 µg/ml in blocking buffer and incubated for 1 hour at room temperature. Following 3× wash with PBS-T, streptavidin-HRP diluted 1:3000 in PBS-T was added and incubated for 1 hour at room temperature. Following 3× wash with PBS-T, the ELISA was developed using TMB substrate (Thermo Pierce Scientific), development stopped by adding 50 µl 1 M sulfuric acid, and the plate read at 405 nm. FIG. 23 shows the standard curve obtained from this experiment, where antibody 2B7 binds to HK but not HKc.

We then determined whether 2B7 could detect HK but not HKc in human plasma. Purified capture antibody 3E8 was immobilized on a 96-well ELISA plate (2 ng/µl in 0.1 M Sodium Bicarbonate buffer pH 9.6 at 4° C. overnight). Wells were washed 3× with PBS-T. Citrated normal human plasma was diluted 1:10 in HEPES-buffered saline (20 mM HEPES, pH 7.4, 140 mM NaCl) and the contact system was fully activated by incubating with 1 mg/ml kaolin (final concentration) or vehicle (for non-activated plasma) for 45 minutes at 37° C. Contact system activation was stopped by incubating both with 10 µg/ml (final concentration) soybean trypsin inhibitor for 15 minutes at 37° C. A gradient of plasma activation was then created by mixing fully activated (100% activated) and non-activated (0% activated) plasma in different proportions. For instance, see Table 6, which provides examples of preparation of plasma with a contact system activation gradient.

TABLE 6

| % Activated Plasma | Activated Plasma 1:300 | Non-Activated Plasma 1:300 | Blocking buffer |
| --- | --- | --- | --- |
| 100% | 60 µl | 0 µl | 540 µl |
| 90% | 54 µl | 6 µl | 540 µl |
| 70% | 42 µl | 18 µl | 540 µl |
| 50% | 30 µl | 30 µl | 540 µl |
| 30% | 18 µl | 42 µl | 540 µl |
| 10% | 6 µl | 54 µl | 540 µl |
| 5% | 3 µl | 57 µl | 540 µl |
| 0% | 0 µl | 60 µl | 540 µl |

Plasma was then further diluted to 1:5000 with blocking buffer (PBS+0.1% Tween-20+1% BSA+0.02% NaN3) and applied to wells for 1 hour at room temperature. Plasma was then removed and the wells washed 3× with PBS-T. Biotinylated detection antibody 2B7 was added (50 µl of 0.05 µg/ml mAb in blocking buffer) and incubated for 1 hour at room temperature. Detection antibody was removed, the plate washed 3× with PBS-T, and 50 µl of streptavidin-HRP applied (1:5000 in PBS-T) for 1 hour at room temperature. Streptavidin-HRP was removed, the plate washed 3× with PBS-T, and 50 µl of TMB substrate (Thermo Pierce Scientific) was added to develop the ELISA. Development was stopped by adding 50 µl of 1 M sulfuric acid, and the plate was read at 405 nm.

FIG. 24 shows that 2B7 can sensitively detect various levels of HK in human plasma, from 0-100%. To test whether 2B7 specifically detected HK and not another plasma protein, the same experiment was performed in HK-depleted human plasma (Affinity Biologicals), where no signal was observed at any level of plasma activation.

AD patient and ND control plasma. We next tested whether our ELISA could detect differences in the levels of intact HK between AD patient and ND control plasma determined previously by Western blot (in FIGS. 1 and 2). The ELISA was performed as described above, except plasma from individual patients or controls was applied to the plate in duplicate at 1:3200 dilution. FIG. 25A shows that intact HK levels were significantly lower in AD patient plasma from Group 1. The levels of intact HK detected by ELISA correlated with intact HK detected by Western blot previously in FIG. 1 C,D (FIG. 25B r=0.85, p<0.0001).

Samples from Group 2 were also tested by ELISA, and intact HK levels were again found to be significantly decreased in AD vs. ND plasma at both 1:3200 and 1:10,000 dilutions (FIGS. 26A and 26B). In Examples 1-7 we demonstrated that intact HK levels as detected by Western blot were correlated with CSF Aβ42 levels in these individuals (FIG. 2D). We show here that HK levels detected by ELISA also correlated with CSF Aβ42 levels (FIG. 26C; r=0.48, p=0.04), indicating that the ELISA is a reliable method for determining intact HK levels in human plasma.

The ELISAs described above measured intact HK in the plasma of AD patients and ND controls. This value can be subtracted from total HK levels determined in the same plasma samples in order to obtain the value for cleaved HK.

While the invention has been described through specific embodiments, routine modifications will be apparent to those skilled in the art and such modifications are intended to be within the scope of the present invention.

What is claimed is:

1. A method for aiding in the diagnosis of Alzheimer's Disease (AD) comprising testing a plasma sample obtained from a human subject suspected of having or at risk for developing AD, wherein the testing comprises using an enzyme-linked immunosorbent assay (ELISA) for high molecular weight kininogen (HK) and cleaved high molecular weight kininogen (HKc) using a capture antibody in the ELISA that is a hamster antibody that binds with specificity to a peptide consisting of the sequence IQSDDDWIPDIQ-IDPNGLSC (SEQ ID NO:6) and determining less HK relative to a normal control, or determining more HKc relative to a normal control, or a combination thereof, to aid in diagnosis of AD.

2. The method of claim 1, wherein the capture antibody is covalently attached to a substrate.

3. The method of claim 1, wherein the ELISA assay further comprises using a detectably labeled detection antibody that binds with specificity to HK and does not bind with specificity to HKc.

* * * * *

```
                            SEQUENCE LISTING

<160> NUMBER OF SEQ ID NOS: 14

<210> SEQ ID NO 1
<211> LENGTH: 644
<212> TYPE: PRT
<213> ORGANISM: homo sapiens

<400> SEQUENCE: 1

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
        50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
                100                 105                 110

Lys Arg Ser Ser Thr Lys Phe Ser Val Ala Thr Gln Thr Cys Gln Ile
            115                 120                 125

Thr Pro Ala Glu Gly Pro Val Val Thr Ala Gln Tyr Asp Cys Leu Gly
        130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
                180                 185                 190

Leu Asn Phe Arg Ile Thr Tyr Ser Ile Val Gln Thr Asn Cys Ser Lys
            195                 200                 205

Glu Asn Phe Leu Phe Leu Thr Pro Asp Cys Lys Ser Leu Trp Asn Gly
        210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
                260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
        290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335
```

-continued

```
Thr Glu Ser Cys Glu Thr Lys Lys Leu Gly Gln Ser Leu Asp Cys Asn
                340                 345                 350

Ala Glu Val Tyr Val Pro Trp Glu Lys Lys Ile Tyr Pro Thr Val
            355                 360                 365

Asn Cys Gln Pro Leu Gly Met Ile Ser Leu Met Lys Arg Pro Gly
    370                 375                 380

Phe Ser Pro Phe Arg Ser Arg Ile Gly Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
    610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 2
<211> LENGTH: 362
<212> TYPE: PRT
<213> ORGANISM: homo sapiens

<400> SEQUENCE: 2

Gln Glu Ser Gln Ser Glu Glu Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
        35                  40                  45

Gly Ser Asp Thr Phe Tyr Ser Phe Lys Tyr Glu Ile Lys Glu Gly Asp
    50                  55                  60
```

```
Cys Pro Val Gln Ser Gly Lys Thr Trp Gln Asp Cys Glu Tyr Lys Asp
 65                  70                  75                  80

Ala Ala Lys Ala Ala Thr Gly Glu Cys Thr Ala Thr Val Gly Lys Arg
                 85                  90                  95

Ser Ser Thr Lys Phe Ser Val Ala Thr Gln Thr Cys Gln Ile Thr Pro
            100                 105                 110

Ala Glu Gly Pro Val Val Thr Ala Gln Tyr Asp Cys Leu Gly Cys Val
        115                 120                 125

His Pro Ile Ser Thr Gln Ser Pro Asp Leu Glu Pro Ile Leu Arg His
    130                 135                 140

Gly Ile Gln Tyr Phe Asn Asn Asn Thr Gln His Ser Ser Leu Phe Met
145                 150                 155                 160

Leu Asn Glu Val Lys Arg Ala Gln Arg Gln Val Val Ala Gly Leu Asn
                165                 170                 175

Phe Arg Ile Thr Tyr Ser Ile Val Gln Thr Asn Cys Ser Lys Glu Asn
            180                 185                 190

Phe Leu Phe Leu Thr Pro Asp Cys Lys Ser Leu Trp Asn Gly Asp Thr
        195                 200                 205

Gly Glu Cys Thr Asp Asn Ala Tyr Ile Asp Ile Gln Leu Arg Ile Ala
    210                 215                 220

Ser Phe Ser Gln Asn Cys Asp Ile Tyr Pro Gly Lys Asp Phe Val Gln
225                 230                 235                 240

Pro Pro Thr Lys Ile Cys Val Gly Cys Pro Arg Asp Ile Pro Thr Asn
                245                 250                 255

Ser Pro Glu Leu Glu Glu Thr Leu Thr His Thr Ile Thr Lys Leu Asn
            260                 265                 270

Ala Glu Asn Asn Ala Thr Phe Tyr Phe Lys Ile Asp Asn Val Lys Lys
        275                 280                 285

Ala Arg Val Gln Val Val Ala Gly Lys Lys Tyr Phe Ile Asp Phe Val
    290                 295                 300

Ala Arg Glu Thr Thr Cys Ser Lys Glu Ser Asn Glu Glu Leu Thr Glu
305                 310                 315                 320

Ser Cys Glu Thr Lys Lys Leu Gly Gln Ser Leu Asp Cys Asn Ala Glu
                325                 330                 335

Val Tyr Val Val Pro Trp Glu Lys Lys Ile Tyr Pro Thr Val Asn Cys
            340                 345                 350

Gln Pro Leu Gly Met Ile Ser Leu Met Lys
        355                 360

<210> SEQ ID NO 3
<211> LENGTH: 9
<212> TYPE: PRT
<213> ORGANISM: homo sapiens

<400> SEQUENCE: 3

Arg Pro Pro Gly Phe Ser Pro Phe Arg
1               5

<210> SEQ ID NO 4
<211> LENGTH: 255
<212> TYPE: PRT
<213> ORGANISM: homo sapiens

<400> SEQUENCE: 4

Ser Ser Arg Ile Gly Glu Ile Lys Glu Glu Thr Thr Val Ser Pro Pro
1               5                   10                  15
```

```
His Thr Ser Met Ala Pro Ala Gln Asp Glu Arg Asp Ser Gly Lys
             20                  25                  30

Glu Gln Gly His Thr Arg Arg His Asp Trp Gly His Glu Lys Gln Arg
         35                  40                  45

Lys His Asn Leu Gly His Gly His Lys His Glu Arg Asp Gln Gly His
         50                  55                  60

Gly His Gln Arg Gly His Gly Leu Gly His Gly His Glu Gln Gln His
65                  70                  75                  80

Gly Leu Gly His Gly His Lys Phe Lys Leu Asp Asp Asp Leu Glu His
                 85                  90                  95

Gln Gly Gly His Val Leu Asp His Gly His Lys His Lys His Gly His
            100                 105                 110

Gly His Gly Lys His Lys Asn Lys Gly Lys Lys Asn Gly Lys His Asn
        115                 120                 125

Gly Trp Lys Thr Glu His Leu Ala Ser Ser Ser Glu Asp Ser Thr Thr
130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
                165                 170                 175

Ser Asp Leu Ile Ala Thr Met Met Pro Pro Ile Ser Pro Ala Pro Ile
            180                 185                 190

Gln Ser Asp Asp Asp Trp Ile Pro Asp Ile Gln Ile Asp Pro Asn Gly
        195                 200                 205

Leu Ser Phe Asn Pro Ile Ser Asp Phe Pro Asp Thr Thr Ser Pro Lys
    210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
                245                 250                 255

<210> SEQ ID NO 5
<211> LENGTH: 206
<212> TYPE: PRT
<213> ORGANISM: homo sapiens

<400> SEQUENCE: 5

His Asn Leu Gly His Gly His Lys His Glu Arg Asp Gln Gly His Gly
1               5                  10                  15

His Gln Arg Gly His Gly Leu Gly His Gly His Glu Gln Gln His Gly
            20                  25                  30

Leu Gly His Gly His Lys Phe Lys Leu Asp Asp Asp Leu Glu His Gln
        35                  40                  45

Gly Gly His Val Leu Asp His Gly His Lys His Lys His Gly His Gly
    50                  55                  60

His Gly Lys His Lys Asn Lys Gly Lys Lys Asn Gly Lys His Asn Gly
65                  70                  75                  80

Trp Lys Thr Glu His Leu Ala Ser Ser Ser Glu Asp Ser Thr Thr Pro
                85                  90                  95

Ser Ala Gln Thr Gln Glu Lys Thr Glu Gly Pro Thr Pro Ile Pro Ser
            100                 105                 110

Leu Ala Lys Pro Gly Val Thr Val Thr Phe Ser Asp Phe Gln Asp Ser
        115                 120                 125

Asp Leu Ile Ala Thr Met Met Pro Pro Ile Ser Pro Ala Pro Ile Gln
    130                 135                 140
```

```
Ser Asp Asp Asp Trp Ile Pro Asp Ile Gln Ile Asp Pro Asn Gly Leu
145                 150                 155                 160

Ser Phe Asn Pro Ile Ser Asp Phe Pro Asp Thr Thr Ser Pro Lys Cys
                165                 170                 175

Pro Gly Arg Pro Trp Lys Ser Val Ser Glu Ile Asn Pro Thr Thr Gln
            180                 185                 190

Met Lys Glu Ser Tyr Tyr Phe Asp Leu Thr Asp Gly Leu Ser
            195                 200                 205

<210> SEQ ID NO 6
<211> LENGTH: 20
<212> TYPE: PRT
<213> ORGANISM: artificial sequence
<220> FEATURE:
<223> OTHER INFORMATION: modified peptide

<400> SEQUENCE: 6

Ile Gln Ser Asp Asp Trp Ile Pro Asp Ile Gln Ile Asp Pro Asn
1               5                   10                  15

Gly Leu Ser Cys
            20

<210> SEQ ID NO 7
<211> LENGTH: 21
<212> TYPE: PRT
<213> ORGANISM: artificial sequence
<220> FEATURE:
<223> OTHER INFORMATION: modified peptide

<400> SEQUENCE: 7

Cys Pro Gly Arg Pro Trp Lys Ser Val Ser Glu Ile Asn Pro Thr Thr
1               5                   10                  15

Gln Met Lys Glu Ser
            20

<210> SEQ ID NO 8
<211> LENGTH: 19
<212> TYPE: PRT
<213> ORGANISM: artificial sequence
<220> FEATURE:
<223> OTHER INFORMATION: modified peptide

<400> SEQUENCE: 8

Cys Asn Ala Glu Val Tyr Val Val Pro Trp Glu Lys Lys Ile Tyr Pro
1               5                   10                  15

Thr Val Asn

<210> SEQ ID NO 9
<211> LENGTH: 11
<212> TYPE: PRT
<213> ORGANISM: artificial sequence
<220> FEATURE:
<223> OTHER INFORMATION: modified peptide

<400> SEQUENCE: 9

Cys Gln Pro Leu Gly Met Ile Ser Leu Met Lys
1               5                   10

<210> SEQ ID NO 10
<211> LENGTH: 16
<212> TYPE: PRT
<213> ORGANISM: artificial sequence
<220> FEATURE:
```

-continued

```
<223> OTHER INFORMATION: modified peptide

<400> SEQUENCE: 10

Ser Ser Arg Ile Gly Glu Ile Lys Glu Glu Thr Thr Val Ser Pro Cys
1               5                   10                  15

<210> SEQ ID NO 11
<211> LENGTH: 17
<212> TYPE: PRT
<213> ORGANISM: artificial sequence
<220> FEATURE:
<223> OTHER INFORMATION: modified peptide

<400> SEQUENCE: 11

His Gly His Lys His Glu Arg Asp Gln Gly His Gly His Gln Arg Gly
1               5                   10                  15

Cys

<210> SEQ ID NO 12
<211> LENGTH: 16
<212> TYPE: PRT
<213> ORGANISM: artificial sequence
<220> FEATURE:
<223> OTHER INFORMATION: modified peptide

<400> SEQUENCE: 12

Lys Lys Asn Gly Lys His Asn Gly Trp Lys Thr Glu His Leu Ala Cys
1               5                   10                  15

<210> SEQ ID NO 13
<211> LENGTH: 15
<212> TYPE: PRT
<213> ORGANISM: homo sapiens

<400> SEQUENCE: 13

Ser Ser Arg Ile Gly Glu Ile Lys Glu Glu Thr Thr Val Ser Pro
1               5                   10                  15

<210> SEQ ID NO 14
<211> LENGTH: 20
<212> TYPE: PRT
<213> ORGANISM: homo sapiens

<400> SEQUENCE: 14

His Asn Leu Gly His Gly His Lys His Glu Arg Asp Gln Gly His Gly
1               5                   10                  15

His Gln Arg Gly
            20
```